United States Patent
Imai

(10) Patent No.: US 11,116,384 B2
(45) Date of Patent: Sep. 14, 2021

(54) ENDOSCOPE SYSTEM CAPABLE OF IMAGE ALIGNMENT, PROCESSOR DEVICE, AND METHOD FOR OPERATING ENDOSCOPE SYSTEM

(71) Applicant: FUJIFILM Corporation, Tokyo (JP)

(72) Inventor: Yoshiro Imai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 602 days.

(21) Appl. No.: 15/973,534

(22) Filed: May 8, 2018

(65) Prior Publication Data
US 2018/0249889 A1 Sep. 6, 2018

Related U.S. Application Data

(63) Continuation of application No. PCT/JP2016/077867, filed on Sep. 21, 2016.

(30) Foreign Application Priority Data

Dec. 22, 2015 (JP) .............................. JP2015-250537

(51) Int. Cl.
*A61B 1/00* (2006.01)
*A61B 1/04* (2006.01)
(Continued)

(52) U.S. Cl.
CPC ........ *A61B 1/00009* (2013.01); *A61B 1/0005* (2013.01); *A61B 1/043* (2013.01);
(Continued)

(58) Field of Classification Search
None
See application file for complete search history.

(56) References Cited

U.S. PATENT DOCUMENTS 5,971,915 A * 10/1999 Yamamoto ......... A61B 1/00193
600/111
6,671,540 B1 * 12/2003 Hochman .............. A61B 5/415
600/431
(Continued)

FOREIGN PATENT DOCUMENTS

JP H03226196 10/1991
JP H03231626 10/1991
(Continued)

OTHER PUBLICATIONS

"International Search Report (Form PCT/ISA/210)" of PCT/JP2016/077867, dated Dec. 20, 2016, with English translation thereof, pp. 1-5.

(Continued)

*Primary Examiner* — Michael J Carey
*Assistant Examiner* — Minqiao Huang
(74) *Attorney, Agent, or Firm* — JCIPRNET

(57) ABSTRACT

The endoscope system includes an image acquiring unit that acquires a first image and a second image, the first image being obtained by imaging an observation target by using first illumination light, the second image being obtained by imaging the observation target by using second illumination light that is different from the first illumination light at a different timing from the first image; an alignment unit that aligns the first image and the second image; and an accuracy changing unit that changes an accuracy of the alignment in accordance with at least a structure of interest to which an attention is paid in the observation target.

11 Claims, 14 Drawing Sheets

(51) Int. Cl.
    *A61B 1/06*     (2006.01)
    *A61B 1/045*    (2006.01)
    *G02B 23/24*    (2006.01)
(52) U.S. Cl.
    CPC ............ *A61B 1/045* (2013.01); *A61B 1/06*
         (2013.01); *A61B 1/0638* (2013.01); *G02B
         23/2484* (2013.01)

(56) References Cited

U.S. PATENT DOCUMENTS

| | | | |
|---|---|---|---|
| 9,547,940 B1* | 1/2017 | Sun ........................ | G06T 7/344 |
| 2003/0236458 A1* | 12/2003 | Hochman ............... | A61B 5/418 |
| | | | 600/431 |
| 2011/0057930 A1* | 3/2011 | Keller .................... | G06T 7/521 |
| | | | 345/419 |
| 2012/0013773 A1 | 1/2012 | Yoshino et al. | |
| 2013/0194403 A1 | 8/2013 | Higuchi | |
| 2013/0211217 A1* | 8/2013 | Yamaguchi .......... | A61B 5/1459 |
| | | | 600/327 |
| 2015/0216398 A1* | 8/2015 | Yang ..................... | G01J 3/0208 |
| | | | 600/109 |
| 2015/0216460 A1* | 8/2015 | Shigeta .................. | A61B 1/05 |
| | | | 600/339 |
| 2015/0272423 A1* | 10/2015 | Ito .......................... | A61B 5/066 |
| | | | 600/476 |
| 2016/0228075 A1* | 8/2016 | Kitamura .............. | A61B 1/00009 |

FOREIGN PATENT DOCUMENTS

| | | |
|---|---|---|
| JP | H0595558 | 4/1993 |
| JP | H05244607 | 9/1993 |
| JP | 2001136540 | 5/2001 |
| JP | 2010227253 | 10/2010 |
| JP | 2011234844 | 11/2011 |
| JP | 2013165//6 | 8/2013 |
| JP | 2013153813 | 8/2013 |
| JP | 2013202189 | 10/2013 |

OTHER PUBLICATIONS

"Written Opinion of the International Searching Authority (Form PCT/ISA/237)" of PCT/JP2016/077867, dated Dec. 20, 2016, with English translation thereof, pp. 1-7.

"Office Action of Japan Counterpart Application," with English translation thereof, dated Mar. 5, 2019, p. 1-p. 5.

"Search Report of Europe Counterpart Application", dated Mar. 7, 2019, p. 1-p. 6.

* cited by examiner

FIG. 4
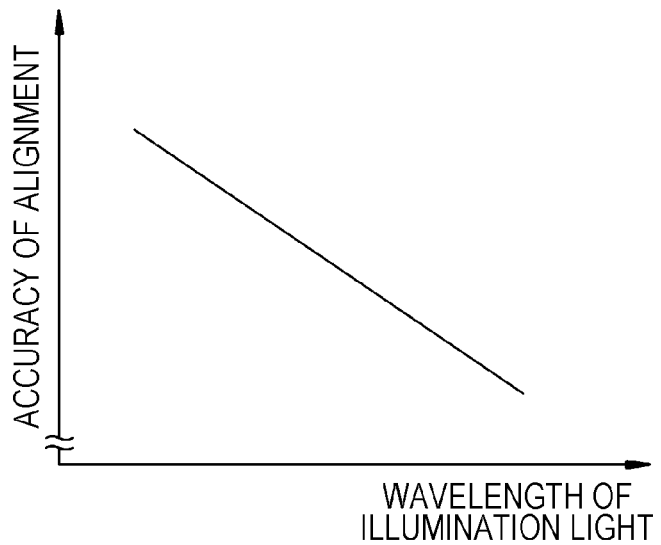
FIG. 5
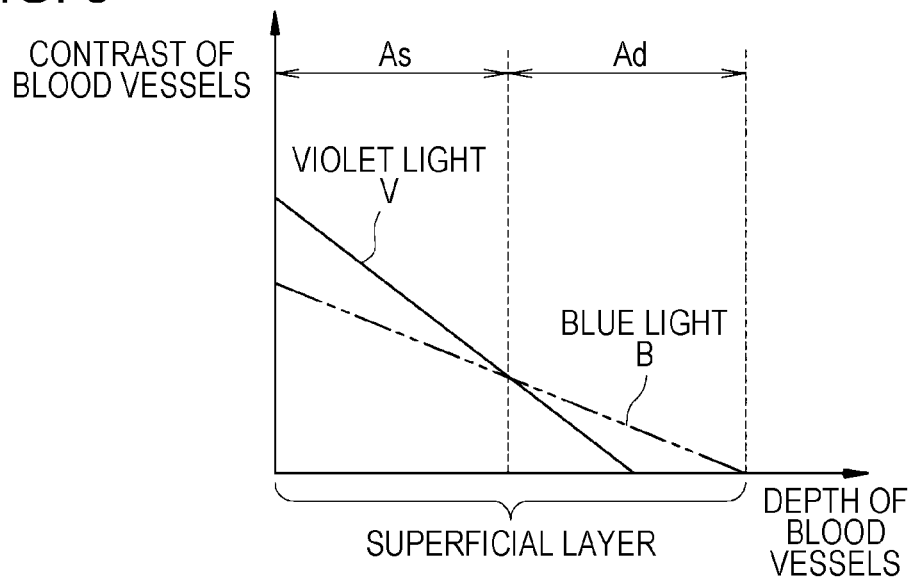
FIG. 6

ENDOSCOPE SYSTEM CAPABLE OF IMAGE ALIGNMENT, PROCESSOR DEVICE, AND METHOD FOR OPERATING ENDOSCOPE SYSTEM

CROSS-REFERENCE TO RELATED APPLICATIONS

This application is a Continuation of PCT International Application No. PCT/JP2016/77867, filed on Sep. 21, 2016, which claims priority under 35 U.S.C. § 119(a) to Japanese Patent Application No. 2015-250537, filed on Dec. 22, 2015. Each of the above application(s) is hereby expressly incorporated by reference, in its entirety, into the present application.

BACKGROUND OF THE INVENTION

1. Field of the Invention

The present invention relates to an endoscope system that aligns two or more images, a processor device, and a method for operating the endoscope system.

2. Description of the Related Art

In the medical field, with an endoscope system including a light source device, an endoscope, and a processor device, an observation target is typically observed and diagnosed by using an almost real-time motion picture. In addition, the following endoscope system is also known. The endoscope system not only is used for natural observation of the observation target, but also is used to obtain an image in which a tissue of interest, such as a blood vessel, or a structure of interest, such as a duct structure (so-called pit pattern), is emphasized by using light beams in an extremely narrow wavelength band (hereinafter referred to as narrow-band light) such as blue and green as illumination light.

In a case of obtaining an image in which the tissue or structure of interest is emphasized, a plurality of images obtained by imaging the observation target at different timings are often used. For example, in order to obtain an image in which a blood vessel or the like is emphasized by using narrow-band light beams such as blue and green as described above, the observation target is sequentially irradiated with a narrow-band light beam of blue and a narrow-band light beam of green, and images obtained by sequentially imaging the observation target by using each of the narrow-band light beams are combined. Besides, a plurality of images obtained by imaging the observation target at different timings may also be used to extract or emphasize a tissue or structure of interest or to calculate biological function information such as an oxygen saturation.

In order to accurately emphasize a tissue of interest or the like, for example, observation targets (subjects) in the plurality of images used are typically aligned (hereinafter simply referred to as "alignment" or "alignment of images"). By aligning the images used, errors due to misalignment of the observation targets in the images (hereinafter referred to as artifacts) are reduced, increasing the accuracy of emphasizing the tissue of interest or the like, for example.

For example, the endoscope system according to JP2011-234844A aligns and combines a normal image captured by using white light and an image captured by using narrow-band light to generate and display an image in which a tissue of interest or the like is emphasized. In addition, the endoscope system according to JP2013-153813A restricts the range for alignment to be within the images at the time of alignment of images to increase the accuracy of alignment.

SUMMARY OF THE INVENTION

In a case of emphasizing a tissue of interest or the like, for example, by using a plurality of images obtained by imaging an observation target at different timings as described above, the plurality of images used are desirably aligned to reduce artifacts. However, the alignment involves a large calculation load and takes time. Accordingly, if highly accurate alignment is performed every time in order to increase the accuracy of emphasis as high as to be used for diagnosis, for example, the frame rate may unfortunately decrease.

It is needless to say that, unless alignment is performed, it is possible to maintain the frame rate at which the observation target can be observed without stress; however, for example, emphasized portions and values of biological function information are less accurate. Accordingly, a physician or the like cannot trust, for example, the emphasis on the tissue of interest or the like and display of the biological function information to make diagnosis. Thus, it is meaningless to, for example, emphasize the tissue of interest or to calculate the biological function information.

An object of the present invention is to provide: an endoscope system that appropriately reduces time for alignment as needed when, for example, emphasizing a tissue of interest or the like by using a plurality of images obtained by imaging an observation target at different timings to achieve both the frame rate and the accuracy of, for example, emphasizing the tissue of interest or the like; a processor device; and a method for operating the endoscope system.

An endoscope system according to the present invention includes an image acquiring unit that acquires a first image and a second image, the first image being obtained by imaging an observation target by using first illumination light, the second image being obtained by imaging the observation target by using second illumination light that is different from the first illumination light at a different timing from the first image; an alignment unit that aligns the first image and the second image; and an accuracy changing unit that changes an accuracy of the alignment in accordance with at least a structure of interest to which an attention is paid in the observation target.

The endoscope system preferably further includes an illumination light selecting unit that selects the first illumination light and the second illumination light in accordance with the structure of interest, and the accuracy changing unit preferably changes the accuracy of the alignment in accordance with the first illumination light, the second illumination light, or a combination of the first illumination light and the second illumination light selected by the illumination light selecting unit.

The accuracy changing unit preferably increases the accuracy of the alignment as the first illumination light, the second illumination light, or the combination of the first illumination light and the second illumination light selected by the illumination light selecting light has a shorter wavelength.

The endoscope system preferably further includes a depth specifying unit that specifies a depth of the structure of interest, and the accuracy changing unit preferably changes the accuracy of the alignment by using the depth specified by the depth specifying unit.

The accuracy changing unit preferably increases the accuracy of the alignment as the depth of the structure of interest specified by the depth specifying unit is shallower.

The endoscope system preferably further includes a movement-amount calculating unit that calculates a movement amount of the observation target by using the first image and the second image, and the accuracy changing unit preferably changes the accuracy of the alignment by using the movement amount.

The accuracy changing unit preferably increases the accuracy of the alignment as the movement amount is smaller.

The endoscope system preferably further includes a blur-amount calculating unit that calculates a blur amount of the first image or the second image, and the accuracy changing unit preferably changes the accuracy of the alignment by using the blur amount.

The accuracy changing unit preferably increases the accuracy of the alignment as the blur amount is smaller.

A processor device of an endoscope system according to the present invention includes an image acquiring unit that acquires a first image and a second image, the first image being obtained by imaging an observation target by using first illumination light, the second image being obtained by imaging the observation target by using second illumination light that is different from the first illumination light at a different timing from the first image; an alignment unit that aligns the first image and the second image; and an accuracy changing unit that changes an accuracy of the alignment in accordance with at least a structure of interest to which an attention is paid in the observation target.

A method for operating an endoscope system according to the present invention includes a step in which an image acquiring unit acquires a first image and a second image, the first image being obtained by imaging an observation target by using first illumination light, the second image being obtained by imaging the observation target by using second illumination light that is different from the first illumination light at a different timing from the first image; a step in which an alignment unit aligns the first image and the second image; and a step in which an accuracy changing unit changes an accuracy of the alignment in accordance with at least a structure of interest to which an attention is paid in the observation target.

With the endoscope system, the processor device, and the method for operating the endoscope system according to the present invention, it is possible to appropriately reduce time for alignment as needed when, for example, emphasizing a tissue of interest or the like by using a plurality of images obtained by imaging an observation target at different timings to achieve both the frame rate and the accuracy of, for example, emphasizing the tissue of interest or the like.

BRIEF DESCRIPTION OF THE DRAWINGS

FIG. 4 is a graph illustrating a relationship between the wavelength of illumination light and the accuracy of alignment;
FIG. 5 is a graph schematically illustrating a relationship between the depth of blood vessels and the contrast of the blood vessels;
FIG. 6 is an explanatory diagram illustrating a method for generating a structure-of-interest emphasized image.

DESCRIPTION OF THE PREFERRED EMBODIMENTS

First Embodiment

Figure 1:
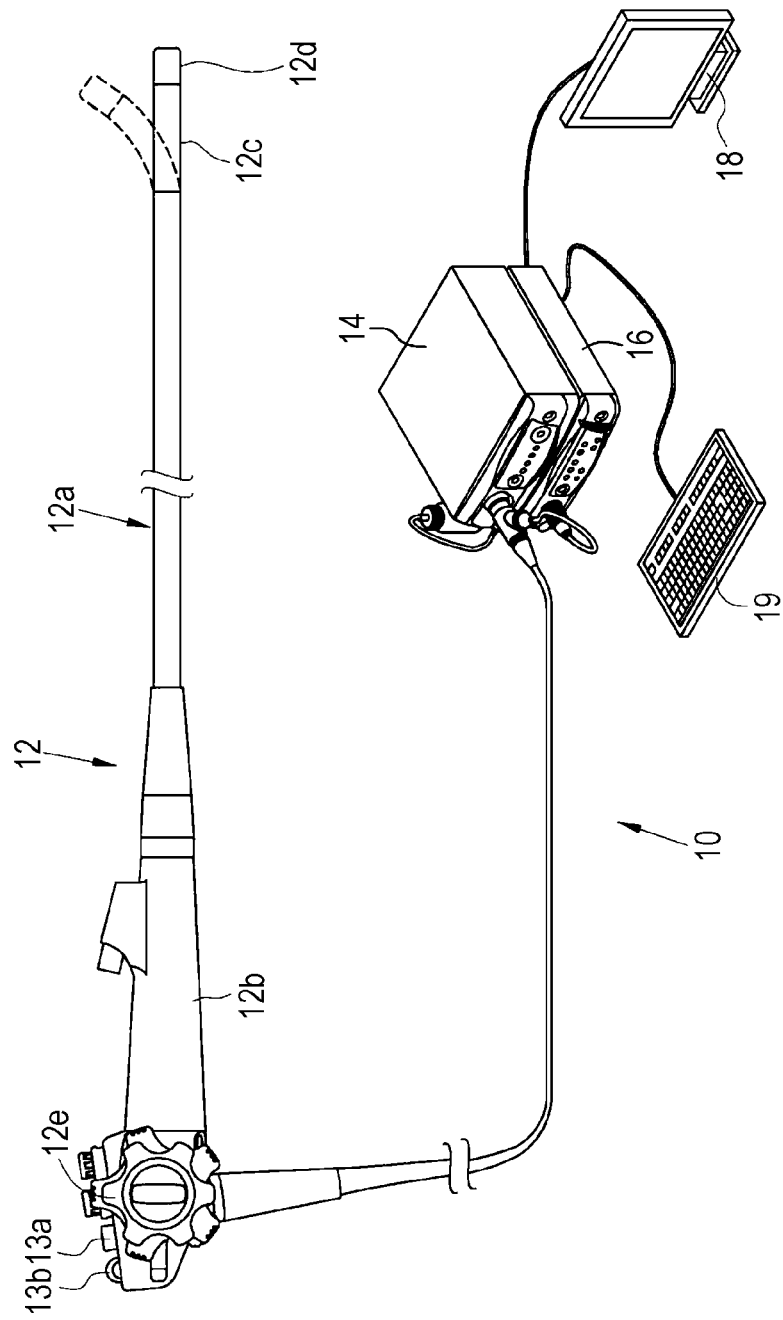
FIG. 1 is an external view of an endoscope system.

As illustrated in FIG. 1, an endoscope system 10 has an endoscope 12, a light source device 14, a processor device 16, a monitor 18, and a console 19. The endoscope 12 is optically connected to the light source device 14 and is electrically connected to the processor device 16. The endoscope 12 has an insertion part 12a to be inserted into a subject, an operating unit 12b provided at the base end portion of the insertion part 12a, and a bending part 12c and a tip part 12d provided at the distal end side of the insertion part 12a. Operation of an angle knob 12e of the operating unit 12b causes the bending part 12c to bend. As a result of the bending of the bending part 12c, the tip part 12d is oriented in a desired direction.

In addition, the operating unit 12b is provided with, in addition to the angle knob 12e, a mode switch 13a and a zoom operating unit 13b. The mode switch 13a is used for operation of switching an observation mode. The endoscope system 10 has a normal observation mode and a special observation mode. The normal observation mode is an observation mode for displaying, on the monitor 18, an image with natural colors (hereinafter referred to as a normal image) obtained by imaging an observation target by using white light as illumination light. The special observation mode is an observation mode for displaying, by using images obtained by imaging an observation target, an image in which a blood vessel at a specific depth among blood vessels included in the observation target is emphasized.

The processor device 16 is electrically connected to the monitor 18 and the console 19. The monitor 18 outputs and displays images in the respective observation modes and image information and the like accompanying the images.

The console 19 serves as a user interface that receives an input operation for setting functions and the like. Note that an external recording unit (omitted from illustration) that records images, image information, and the like may be connected to the processor device 16.

Figure 2:
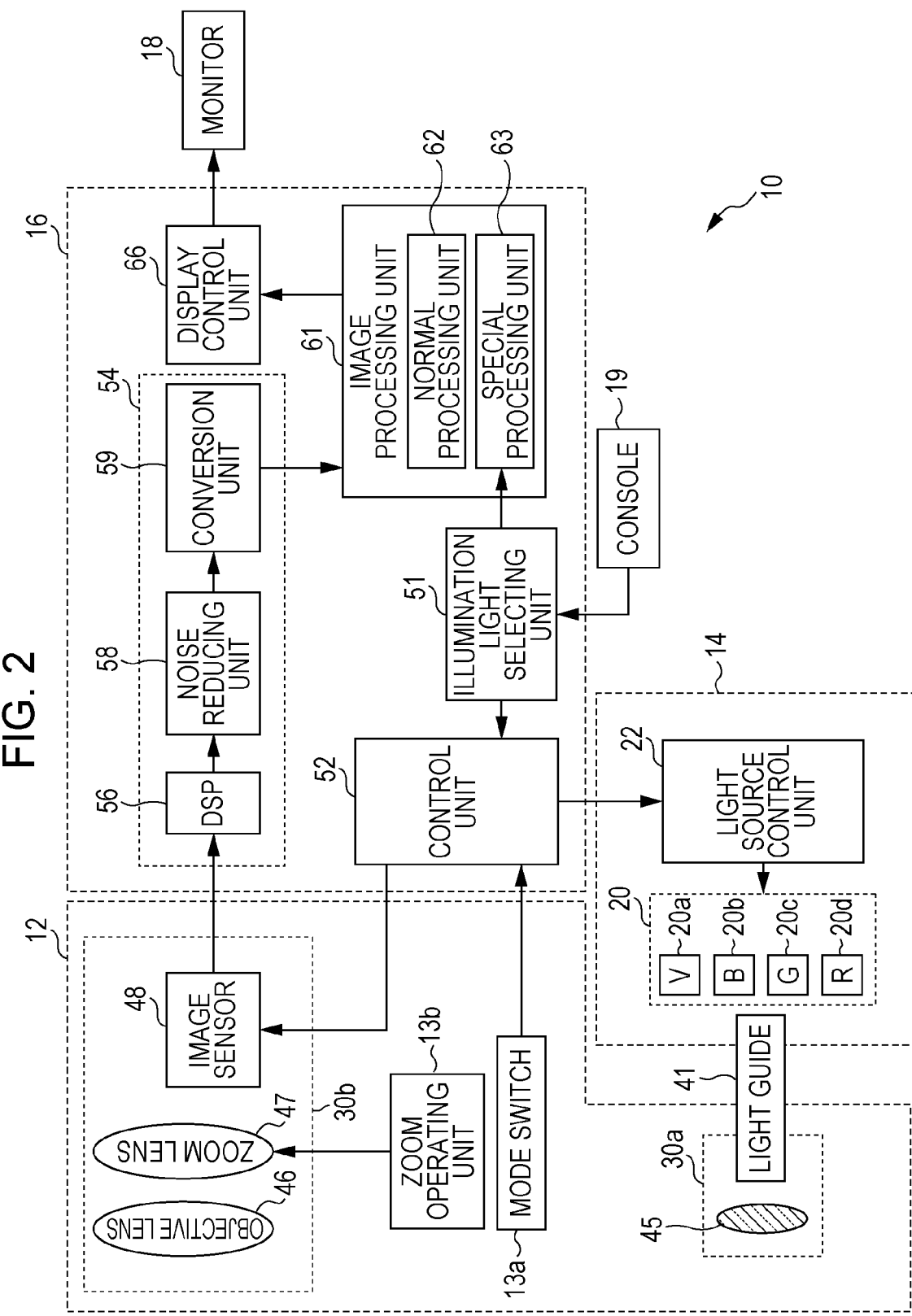
FIG. 2 is a block diagram of the endoscope system.

As illustrated in FIG. 2, the light source device 14 includes a light source unit 20 that emits illumination light and a light source control unit 22 that controls driving of the light source unit 20.

The light source unit 20 includes four light sources, which are a V light source 20a, a B light source 20b, a G light source 20c, and an R light source 20d. In this embodiment, the V light source 20a, the B light source 20b, the G light source 20c, and the R light source 20d are each a light emitting diode (LED). For the light source unit 20, instead of these LEDs, a combination of a laser diode (LD), a fluorescent body, and a band limiting filter, a combination of a lamp such as a xenon lamp and a band limiting filter, and the like can be used.

The V light source 20a is a violet light source that emits violet light V with a center wavelength of about 405 nm and a wavelength band of about 380 nm to 420 nm. The B light source 20b is a blue light source that emits blue light B with a center wavelength of about 460 nm and a wavelength band of about 420 nm to 500 nm. The G light source 20c is a green light source that emits green light G with a wavelength band of about 480 nm to 600 nm. The R light source 20d is a red light source that emits red light R with a center wavelength of about 620 nm to 630 nm and a wavelength band of about 600 nm to 650 nm. Note that the center wavelengths of the V light source 20a and the B light source 20b have a margin of about ±5 nm to ±10 nm.

The light source control unit 22 independently controls timings for turning on and off the respective light sources 20a to 20d constituting the light source unit 20, light emission amounts at the time of turning on, and the like. In the normal observation mode, the light source control unit 22 turns on all of the V light source 20a, the B light source 20b, the G light source 20c, and the R light source 20d. Thus, in the normal observation mode, the illumination light is white light including the violet light V, the blue light B, the green light G, and the red light R.

On the other hand, in the special observation mode, first illumination light and second illumination light different from the first illumination light are selected by setting and used. Thus, in the special observation mode, the light source control unit 22 controls the light sources 20a to 20d of the respective colors between an emission pattern in which the first illumination light is emitted and an emission pattern in which the second illumination light is emitted.

For example, if the first illumination light and the second illumination light selected by setting is the violet light V and the blue light B, the light source control unit 22 alternately repeats an emission pattern in which only the V light source 20a is turned on and an emission pattern in which only the B light source 20b is turned on. In addition, if the first illumination light and the second illumination light selected by setting is the blue light B and the green light G, the light source control unit 22 alternately repeats an emission pattern in which only the B light source 20b is turned on and an emission pattern in which only the G light source 20c is turned on.

Of course, the red light R can be used as the first illumination light or the second illumination light. In addition, single-color light emitted by using any one of the light sources 20a to 20d of the respective colors can be used as the first illumination light or the second illumination light, and furthermore, light emitted by turning on two or more light sources among the light sources 20a to 20d of the respective colors can also be used as the first illumination light or the second illumination light. In a case in which the first illumination light or the second illumination light is emitted by turning on a plurality of light sources, by changing the whole spectrum by adjusting the balance of light amounts of light sources to be turned on, light having various colors can be used as the first illumination light or the second illumination light even if the combination of the light sources to be turned on is the same. Of light having each color emitted from any of the light sources 20a to 20d of the respective colors, light in which a part of the wavelength band or the light amount is limited by using a band limiting filter can also be used as the first illumination light or the second illumination light. Therefore, "different" illumination light herein means at least one of the wavelength band or the spectrum is not the same when two illumination light beams are compared with each other.

Illumination light emitted from the light source unit 20 enters a light guide 41. The light guide 41 is incorporated in the endoscope 12 and a universal cord (cord connecting the endoscope 12, the light source device 14, and the processor device 16), and the illumination light propagates therethrough to the tip part 12d of the endoscope 12. Note that a multi-mode fiber can be used as the light guide 41. As an example, a small-diameter fiber cable having a core diameter of 105 μm, a clad diameter of 125 μm, and a diameter of Ø 0.3 to 0.5 mm including a protective layer serving as an outer skin can be used.

The tip part 12d of the endoscope 12 is provided with an illumination optical system 30a and an imaging optical system 30b. The illumination optical system 30a has an illumination lens 45, and an observation target is irradiated with illumination light through the illumination lens 45. The imaging optical system 30b has an objective lens 46, a zoom lens 47, and an image sensor 48. The image sensor 48 images the observation target by using, for example, reflected light or scattered light (including fluorescence emitted from the observation target or fluorescence caused by medicine that is, for example, given to the observation target) of illumination light returning from the observation target through the objective lens 46 and the zoom lens 47. Note that the zoom lens 47 is moved by operating the zoom operating unit 13b and zooms in or zooms out the observation target imaged by the image sensor 48.

The image sensor 48 is a color sensor of the primary color system and has three types of pixels: a B pixel (blue pixel) provided with a blue color filter that mainly transmits light of a violet to blue wavelength band; a G pixel (green pixel) provided with a green color filter that mainly transmits light of a green wavelength band; and an R pixel (red pixel) provided with a red color filter that mainly transmits light of a red wavelength band. Accordingly, when the observation target is imaged by the image sensor 48, three types of images, which are a B image (blue image), a G image (green image), and an R image (red image), are obtained.

In the normal observation mode, since the illumination light is white light, as described above, each of the B image, the G image, and the R image is obtained. Specifically, the B pixel images the observation target by receiving light of the violet to blue wavelength band from reflected light or the like of the white light and outputs the B image. The G pixel receives light of the green wavelength band and outputs the G image, and the R pixel receives light of the red wavelength band and outputs the R image.

On the other hand, in the special observation mode, the illumination light is alternately switched between the first illumination light and the second illumination light. Accordingly, an image of the BGR colors obtained by imaging the observation target by using the first illumination light (hereinafter this image will be referred to as a first image) and an image of the BGR colors obtained by imaging the observation target by using the second illumination light at a different timing from the first image (hereinafter this image will be referred to as a second image) are obtained. For example, in a case in which the violet light V is used as the first illumination light and the blue light B is used as the second illumination light, a B image corresponding to reflected light or the like of the violet light V (hereinafter this image will be referred to as a V image) is the first image, and a B image corresponding to the blue light B is the second image.

Note that a charge coupled device (CCD) sensor or a complementary metal oxide semiconductor (CMOS) sensor can be used as the image sensor 48. In addition, although the image sensor 48 according to this embodiment is a color sensor of the primary color system, a color sensor of the complementary color system can also be used. The color sensor of the complementary color system has, for example, a cyan pixel provided with a cyan color filter, a magenta pixel provided with a magenta color filter, a yellow pixel provided with a yellow color filter, and a green pixel provided with a green color filter. Images obtained from the pixels of the above respective colors when using the color sensor of the complementary color system can be converted into a B image, a G image, and an R image through complementary color-to-primary color conversion. In addition, instead of the color sensor, a monochrome sensor without a color filter can be used as the image sensor 48. In this case, by sequentially imaging the observation target by using illumination light of the respective colors such as BGR, images of the above respective colors can be obtained.

The processor device 16 has an illumination light selecting unit 51, a control unit 52, an image acquiring unit 54, an image processing unit 61, and a display control unit 66. For example, the processor device 16 has a central processing unit (CPU), and the CPU serves as the illumination light selecting unit 51, the control unit 52, the image acquiring unit 54, the image processing unit 61, and the display control unit 66.

On the basis of setting or the like that has been input from the console 19, the illumination light selecting unit 51 selects the first illumination light and the second illumination light to be used in the special observation mode in accordance with a structure of interest to which attention is paid in the observation target. The structure of interest is a tissue, structure, or the like to which attention is paid for the purpose of observation for diagnosis in a structure or the like such as a tissue pit pattern like a blood vessel included in the observation target. For example, a blood vessel in a specific depth range among blood vessels included in the observation target is the structure of interest.

When the wavelengths of the first illumination light and the second illumination light suitable for observation or the like of the structure of interest is set and input by using the console 19, the illumination light selecting unit 51 selects, as the first illumination light and the second illumination light, suitable illumination light beams close to the set and input wavelengths of the first illumination light and the second illumination light from among light beams that is selectable by the system. For example, in a case in which, among submucosal blood vessels in a relatively shallow depth range (hereinafter referred to as superficial blood vessels), a blood vessel in a particularly shallow depth range (hereinafter referred to as a most superficial blood vessel) is the structure of interest, the wavelength (e.g., 400 nm), the wavelength band, the color, or the like of the first illumination light and the wavelength (e.g., 450 nm), the wavelength band, the color, or the like of the second illumination light suitable for observation of the most superficial blood vessel are set and input. If the endoscope system 10 can freely select the first illumination light and the second illumination light as the system from among four types of light, which are the violet light V, the blue light B, the green light G, and the red light R, the illumination light selecting unit 51 selects the violet light V as the first illumination light and the blue light B as the second illumination light in accordance with the setting and inputting. Since the setting and inputting is made in accordance with the structure of interest, the selection of the first illumination light and the second illumination light as described above equals to selection of the first illumination light and the second illumination light in accordance with the structure of interest.

In response to an input of a mode switching signal from the mode switch 13a, the control unit 52 inputs a control signal to the light source control unit 22 and the image sensor 48 to switch the observation mode. In addition, in the special observation mode, the control unit 52 inputs a control signal corresponding to the first illumination light and the second illumination light selected by the illumination light selecting unit 51 to the light source control unit 22. Thus, the light source control unit 22 emits the first illumination light and the second illumination light selected by the illumination light selecting unit 51 by using the light source unit 20. Besides, the control unit 52 controls synchronization of an illumination-light irradiation timing and an imaging timing, for example.

The image acquiring unit 54 acquires images of the respective colors from the image sensor 48. Specifically, in the normal observation mode, the image acquiring unit 54 acquires the B image, the G image, and the R image from the image sensor 48. On the other hand, in the special observation mode, the image acquiring unit 54 acquires, from the image sensor 48, the first image obtained by imaging the observation target by using the first illumination light and the second image obtained by imaging the observation target by using the second illumination light different from the first illumination light at a different timing from the first image. For example, in a case in which the first illumination light is the violet light V and the second illumination light is the blue light B, the image acquiring unit 54 sequentially acquires the V image and the B image.

In addition, the image acquiring unit 54 has a digital signal processor (DSP) 56, a noise reducing unit 58, and a conversion unit 59, and performs various kinds of processing on the acquired images by using these units.

The DSP 56 performs various kinds of processing on the acquired images, such as defect correction processing, offset processing, gain correction processing, linear matrix processing, gamma conversion processing, demosaicing processing, and YC conversion processing, as needed.

The defect correction processing is for correcting the pixel value of a pixel corresponding to a defective pixel of the image sensor 48. The offset processing is for setting an accurate zero level by reducing a dark current component from an image subjected to the defect correction processing. The gain correction processing is for adjusting the signal level of each image by multiplying the image subjected to the offset processing by a gain. The linear matrix processing increases the color reproducibility of an image subjected to the offset processing, and the gamma conversion processing is for adjusting the brightness and saturation of an image subjected to the linear matrix processing. The domosaicing processing (also referred to as isotropic processing or synchronization processing) is for interpolating the pixel value of a lacking pixel and is performed on an image subjected to the gamma conversion processing. The lacking pixel is a pixel without a pixel value as a result of arrangement of a pixel of another color in the image sensor 48 for the array of the color filters. For example, since the B image is obtained by imaging the observation target by using the B pixel, there are no pixel values of pixels at positions corresponding to the G pixel and the R pixel in the image sensor 48. The demosaicing processing interpolates the B image and generates the pixel values of the pixels at positions corresponding to the G pixel and the R pixel in the image sensor 48. The YC conversion processing converts an image subjected to the demosaicing processing into a luminance channel Y, a chroma channel Cb, and a chroma channel Cr.

The noise reducing unit 58 performs noise reducing processing on the luminance channel Y, the chroma channel Cb, and the chroma channel Cr, by using, for example, a moving average method or a median filter method. The conversion unit 59 re-converts the luminance channel Y, the chroma channel Cb, and the chroma channel Cr, which have been subjected to the noise reducing processing, into images of BGR colors again.

The image processing unit 61 has a normal processing unit 62 and a special processing unit 63. The normal processing unit 62 operates in the normal observation mode and performs color converting processing, color emphasizing processing, and structure emphasizing processing on the images of BGR colors to generate a normal image. In the color converting processing, the images of BGR colors are subjected to 3×3 matrix processing, gradation transformation processing, three-dimensional look-up table (LUT) processing, and the like. The color emphasizing processing is for emphasizing the colors in an image, and the structure emphasizing processing is, for example, for emphasizing a tissue or a structure of the observation target, such as a blood vessel or a pit pattern. The display control unit 66 sequentially acquires the normal image from the normal processing unit 62 and converts the acquired normal image into an image in a format suitable for display to sequentially output and display the image to/on the monitor 18. Thus, in the normal observation mode, a physician or the like can observe the observation target by using a motion picture of the normal image.

Figure 3:
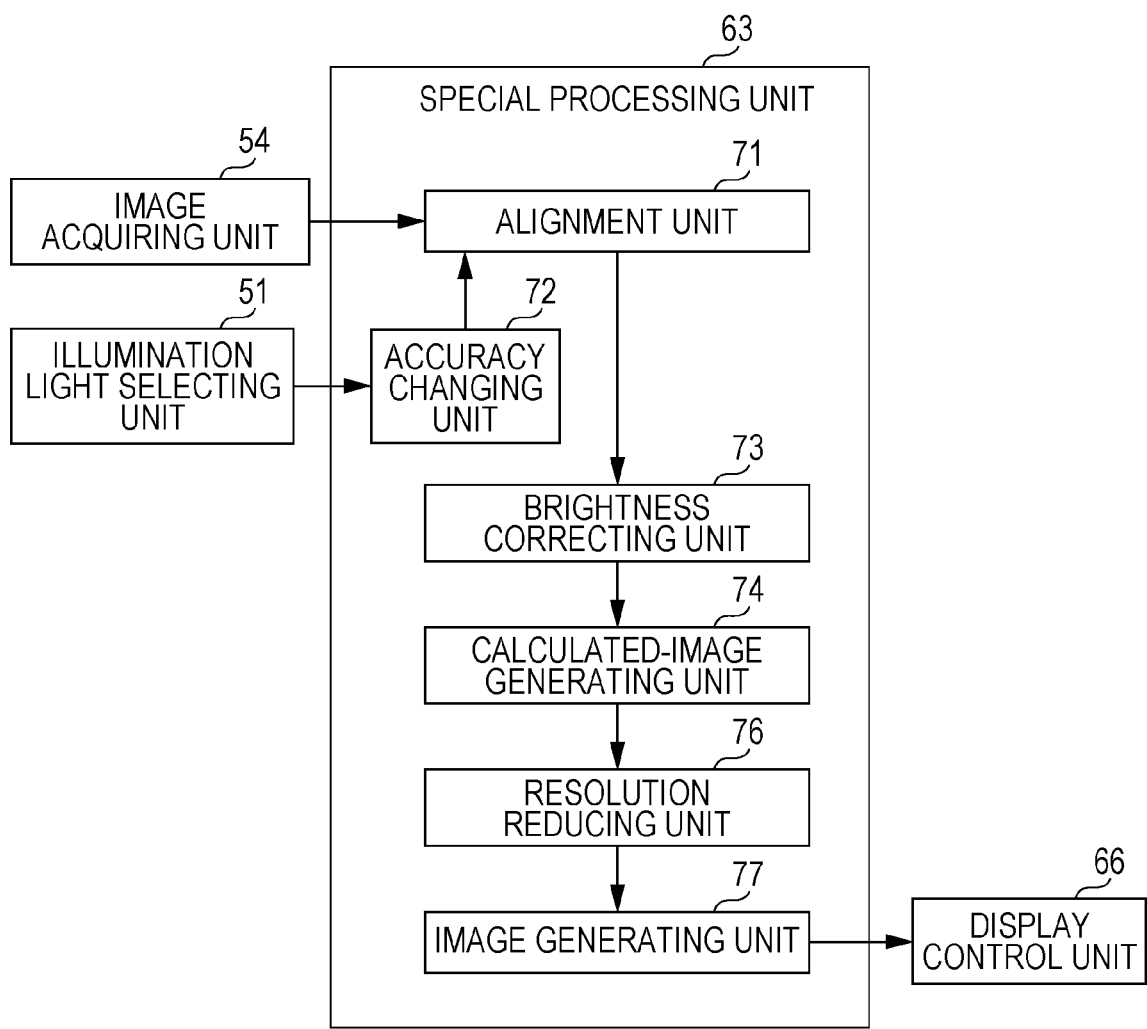
FIG. 3 is a block diagram of a special processing unit.

The special processing unit 63 operates in the special observation mode, and generates, by using the images acquired in the special observation mode, an image representing a blood vessel at a specific depth (e.g., specific depth based on the mucosal surface of the observation target) by using a color that is different from the colors of the other blood vessels. As illustrated in FIG. 3, the special processing unit 63 includes an alignment unit 71, an accuracy changing unit 72, a brightness correcting unit 73, a calculated image generating unit 74, a resolution reducing unit 76, and an image generating unit 77.

The alignment unit 71 aligns the first image and the second image. The alignment of the first image and the second image (hereinafter simply referred to as alignment) is a process to make the positions (coordinates) of corresponding portions of the observation target represented in the first image and the observation target represented in the second image substantially correspond to each other. Specifically, the alignment can be performed by estimating a motion vector of the observation target represented in both images by performing matching between the first image and the second image, and by deforming, on the basis of the estimated motion vector, at least one of the first image or the second image.

The accuracy of the alignment performed by the alignment unit 71 is changeable. Specifically, by changing the density of the estimated motion vector (so-called grating density), the alignment unit 71 can change the accuracy of the alignment. The higher the estimated motion vector density (the larger the number of the motion vectors), the higher the accuracy of the alignment. For example, the accuracy of the alignment is higher when the motion vector is estimated for each one pixel than when the motion vector is estimated for each two pixels. In addition, the alignment unit 71 changes the accuracy for obtaining the final point of the motion vector, and can consequently change the accuracy of the alignment. For example, when the final point of the motion vector is obtained at the sub-pixel level, the accuracy of the alignment is increased. Similarly, if a case in which the final point of the motion vector is obtained at the ⅛-sub-pixel level is compared with a case in which the final point of the motion vector is obtained at the ½-sub-pixel level, the accuracy of the alignment is higher when the final point of the motion vector is obtained at the ⅛-sub-pixel level. In addition, in a case in which the matching between images is performed for each level after decomposition to multi-resolutions (for each decomposed resolution), matching in a high-resolution level can be skipped to change the accuracy of the alignment.

The accuracy changing unit 72 changes the accuracy of the alignment performed by the alignment unit 71 in accordance with, at least, the structure of interest in the observation target. In this embodiment, the accuracy changing unit 72 sets the accuracy of the alignment in accordance with the first illumination light, the second illumination light, or the combination of the first illumination light and the second illumination light (hereinafter referred to as selected illumination light) selected by the illumination light selecting unit 51. Since the illumination light selecting unit 51 selects the first illumination light and the second illumination light in accordance with the structure of interest, changing the accuracy of the alignment in accordance with the selected illumination light is the same as changing the accuracy of the alignment in accordance with the structure of interest.

To "change the accuracy of the alignment in accordance with the first illumination light" means to change the accuracy of the alignment on the basis of an average wavelength or the like taking into account the center wavelength, the peak wavelength, the range of wavelength band, or the spectrum of the first illumination light. Similarly, to "change the accuracy of the alignment in accordance with the second illumination light" means to change the accuracy of the alignment on the basis of an average wavelength or the like taking into account the center wavelength, the peak wavelength, the range of wavelength band, or the spectrum of the second illumination light. To "change the accuracy of the alignment in accordance with the combination of the first illumination light and the second illumination light" means to change the accuracy of the alignment on the basis of a statistic (average, median, or the like) of the wavelength or the like taking into account the center wavelengths, the peak wavelengths, the ranges of wavelength hands, or spectrums of the first illumination light and the second illumination light.

The shorter the wavelength of the selected illumination light (the first illumination light, the second illumination light, or the combination of the first illumination light and the second illumination light), the higher the accuracy of the alignment set by the accuracy changing unit 72. The expression "the first illumination light has a short wavelength" means that the average wavelength or the like taking into account the center wavelength, the peak wavelength, the range of wavelength band, or the spectrum of the first illumination light is short. Similarly, the expression "the second illumination light has a short wavelength" means that the average wavelength or the like taking into account the center wavelength, the peak wavelength, the range of wavelength band, or the spectrum of the second illumination light is short. The expression "the combination of the first illumination light and the second illumination light has a short wavelength" means that the statistic (average, median, standard deviation, or the like) of the wavelength or the like taking into account the center wavelengths, the peak wavelengths, the ranges of wavelength bands, or spectrums of the first illumination light and the second illumination light is short or small.

It is assumed that the accuracy changing unit 72 determines the accuracy of the alignment in accordance with the first illumination light from among the above three patterns. In this case, for example, if a case in which the first illumination light is the violet light V is compared with a case in which the second illumination light is the blue light B, the center wavelength or the like of the blue light B is shorter than that of the violet light V. Accordingly, the accuracy changing unit 72 sets a higher accuracy of the alignment when the violet light V is used as the first illumination light than when the blue light B is used. The accuracy changing unit 72 determines the accuracy of the alignment similarly in accordance with the second illumination light.

It is assumed that the accuracy changing unit 72 determines the accuracy of the alignment in accordance with the combination of the first illumination light and the second illumination light from among the above three patterns. In this case, for example, if a case in which the combination of the first illumination light and the second illumination light is the violet light V and the blue light B is compared with a case in which the combination of the first illumination light and the second illumination light is the blue light B and the green light G, the average of the center wavelengths is shorter in the case of the combination of the violet light V and the blue light B than in a case of the combination of the blue light B and the green light G. Accordingly, the accuracy changing unit 72 sets a higher accuracy of the alignment when the violet light V and the blue light B are used as the first illumination light and the second illumination light than when the blue light B and the green light G are used as the first illumination light and the second illumination light.

In either case, for example, as illustrated in FIG. 4, the accuracy changing unit 72 sets a higher accuracy of the alignment as the illumination light used in the special observation mode has a shorter wavelength as a whole. This corresponds to setting of a lower accuracy of the alignment as the illumination light to be used in the special observation mode has a longer wavelength as a whole.

Typically, in a case in which the observation target is a living body, the tissues, structures, and the like tend to be thinner and smaller as the submucosal depth is smaller and tend to be thicker and larger as the submucosal depth is larger. In addition, the degree of reach in the observation target is smaller as the light has a shorter wavelength and is larger as the light has a longer wavelength. Thus, with light having a shorter wavelength, structures or the like at a shallow position under the mucous membrane are likely to be observed; with light having a longer wavelength, structures or the like at a deeper position under the mucous membrane are likely to be observed. Accordingly, a case in which the illumination light to be used in the special observation mode has a short wavelength as a whole corresponds to a case in which almost all of the structures of interest are thin and small tissues and structures, and thus, even a slight misalignment between the first image and the second image is likely to generate an artifact that is not negligible in calculations and the like performed later. In contrast, a case in which the illumination light to be used in the special observation mode has a long wavelength as a whole corresponds to a case in which almost all of the structures of interest are thick and large tissues and structures, and thus, even if the first image and the second image are slightly misaligned, the artifact is relatively small. In this case, by observing the observation target by using a motion picture in particular, almost no disturbance of images due to the artifact or the like is visually recognized.

From the above, by changing the accuracy of the alignment as described above in accordance with the wavelength or the like of the illumination light to be used in the special observation mode (that is, the type of structure of interest), the accuracy changing unit 72 reduces the processing load of the alignment unit 71 as needed to complete the alignment process in a short period of time. This facilitates maintenance of the frame rate of images generated and displayed in the special observation mode.

Note that the changing of the accuracy of the alignment includes determination as to whether the alignment is to be performed. That is, if the accuracy of the alignment is decreased, the accuracy changing unit 72 determines that the alignment is not to be performed so as to skip the process performed by the alignment unit 71, preventing the alignment from being performed. In addition, if the accuracy of the alignment is changed in accordance with the above determination, the accuracy in a case in which the alignment is to be performed may be set to a fixed accuracy or can be set in accordance with the wavelength of the selected illumination light as in the above description.

The brightness correcting unit 73 corrects the brightness of at least one of the first image or the second image aligned by the alignment unit 71, and sets a specific brightness ratio between the first image and the second image. For example, the brightness correcting unit 73 may perform gain correction on at least one of the first image or the second image by using a light-amount ratio between the first illumination light and the second illumination light to correct the relative brightness of the first image and the second image.

Since the light amount of the first illumination light at the time of obtaining the first image and the light amount of the second illumination light at the time of obtaining the second image are known when the first image and the second image are obtained, the light-amount ratio between the first illumination light and the second illumination light is known at the stage in which the brightness correcting unit 73 corrects the brightness. Accordingly, for example, if the first illumination light and the second illumination light are the violet light V and the blue light B, respectively, with a light-amount ratio therebetween being 2:1, the brightness correcting unit 73 halves the brightness of the V image (first image) by gain correction, or doubles the brightness of the B image (second image) by gain correction, so as to set the brightness ratio between the V image (first image) and the B image (second image) to 1:1 (specific ratio).

In addition, the average luminance of the first image substantially corresponds to the brightness of the mucous membrane of the observation target represented in the first image. Similarly, the average luminance of the second image substantially corresponds to the brightness of the mucous membrane of the observation target represented in the second image. Accordingly, as described above, instead of using the ratio between the first illumination light and the second illumination light, the brightness correcting unit 73 can calculate the average luminances of the first image and the second image, and can perform, by using a ratio of the average luminances, gain correction on at least one of the first image or the second image to correct the relative brightness between the first image and the second image to a specific ratio.

The calculated image generating unit 74 performs calculation by using the first image and the second image with corrected brightness to generate a calculated image $\Delta$. Specifically, the calculated image generating unit 74 generates a calculated image representing the difference or ratio between the first image and the second image. In this embodiment, the calculated image generating unit 74 performs logarithmic transformation on the first image and the second image to generate the calculated image $\Delta$ representing the difference between the first image and the second image that are subjected to the logarithmic transformation (more specifically, the calculated image $\Delta$ is obtained by subtracting the first image from the second image). In a case in which the first image and the second image are used without logarithmic transformation, the calculated image $\Delta$ representing the ratio between the first image and the second image (more specifically, the ratio of the first image to the second image) is generated. The pixel value of each pixel in the first image and the second image represents a light receiving amount, but after the logarithmic transformation, the pixel value represents the concentration. Accordingly, a stable calculation result can be obtained irrespective of the illuminance of the illumination light at the time of obtaining each image.

As described above, generation of the calculated image $\Delta$ by the calculated image generating unit 74 corresponds to emphasizing a blood vessel at a specific depth by using the first image and the second image. For example, as illustrated in FIG. 5, if the violet light V and the blue light B are used as the first illumination light and the second illumination light, superficial blood vessels (blood vessels in all depth ranges As and Ad) are substantially observable with either illumination light. However, the violet light V has a smaller degree of reach due to a shorter wavelength than that of the blue light B. Accordingly, in a case in which the violet light V is used as the illumination light, only blood vessels in the relatively shallow depth range As under the mucous membrane are displayed compared with a case in which the blue light B is used as the illumination light. Instead, the contrast of the blood vessels in the depth range As (ratio of a reflected light amount from the blood vessels to a reflected light amount from a peripheral mucous membrane) is larger than that when using the blue light B as the illumination light. In contrast, the blue light B has a larger degree of reach as the wavelength is longer than that of the violet light V. Accordingly, if the blue light B is used as the illumination light, blood vessels in the relatively deep depth range Ad can also be displayed compared with a case in which the violet light V is used as the illumination light. Instead, the contrast of the blood vessels in the shallower depth range As is smaller than that when using the violet light V.

Accordingly, if the calculated image $\Delta$ is generated by subtracting, from the V image obtained by using the violet light V as the illumination light, the B image obtained by using the blue light B as the illumination light, in this calculated image $\Delta$, the pixel value of each pixel representing a most superficial blood vessel in the depth range As, which is a particularly shallow range under the mucous membrane, among the superficial blood vessels, has a large value (white), and the pixel value of each pixel representing a blood vessel in the depth range Ad, which is deep, among the superficial blood vessels, has a small value (black). Accordingly, if the structure of interest is a most superficial blood vessel, by using the violet light V as the first illumination light and the blue light B as the second illumination light, in the calculated image $\Delta$ generated by subtracting the B image from the V image, the most superficial blood vessel in the specific depth range As is emphasized.

Note that, in the calculated image $\Delta$ generated by subtracting the V image from the B image, the pixel value of each pixel representing the most superficial blood vessel in the depth range As has a small value (black), and the pixel value of each pixel representing a blood vessel in the depth range Ad has a large value (white). Accordingly, even in a case in which the combination of the violet light V and the blue light B is used as the first illumination light and the second illumination light as in the above case, by using the blue light B as the first illumination light and the violet light V as the second illumination light, in the calculated image $\Delta$ generated by subtracting the B image from the V image, the blood vessel in the specific depth range Ad is emphasized.

When the calculated image generating unit 74 generates the calculated image $\Delta$ as described above, in addition to an error as a result of a low calculation accuracy of the calculated image generating unit 74, an artifact as a result of a low accuracy of the alignment of the first image and the second image is generated. Since the calculation accuracy of the calculated image generating unit 74 is constant, a substantial error, which is variable, of the calculated image $\Delta$ is an artifact as a result of a low accuracy of the alignment of the first image and the second image. The artifact as a result of a low accuracy of the alignment of the first image and the second image is controlled by the accuracy changing unit 72, and as a result, the accuracy changing unit 72 controls the generation accuracy of the calculated image $\Delta$.

The resolution reducing unit 76 is a so-called low-pass filter (hereinafter referred to as an LPF) and reduces the resolution of the calculated image $\Delta$. The processing intensity for reducing the resolution of the calculated image $\Delta$ by the resolution reducing unit 76 is determined by the cut-off frequency of the LPF. The cut-off frequency of the LPF is set in advance, and the resolution is reduced to be, at least, lower than the resolution of the original calculated image $\Delta$.

By using either one of the first image and the second image and the calculated image $\Delta$ with a reduced resolution, the image generating unit 77 generates an image having the luminance channel Y and the two chroma channels Cb and Cr. Specifically, the image generating unit 77 assigns either of the first image and the second image having a higher contrast of the structure of interest to the luminance channel Y and assigns the calculated image $\Delta$ with a reduced resolution to the two chroma channels Cb and Cr, thereby generating a structure-of-interest emphasized image in which the structure of interest is emphasized with color.

For example, in a case in which the structure of interest is a most superficial blood vessel, the violet light V and the blue light B are respectively used as the first illumination light and the second illumination light, as a result of comparison between the V image (first image) and the B image (second image), the contrast of the most superficial blood vessel, which is the structure of interest, has a relatively higher contrast in the V image. Accordingly, as illustrated in FIG. 6, the image generating unit 77 assigns the V image having a relatively higher contrast of the most superficial blood vessel to the luminance channel Y. In addition, when assigning the calculated image Δ to the chroma channels Cb and Cr, multiplication by a factor α (e.g., α=0.169) and a factor β (e.g., (β=0.5) is performed, thereby setting the same color as the color of images displayed by another endoscope system that emphasizes and observes a superficial blood vessel or the like. The thus generated structure-of-interest emphasized image has substantially the same color as a whole as images in which a blood vessel or the like is emphasized by a conventional endoscope system, but the most superficial blood vessel, which is the structure of interest, is emphasized by using a color different from the colors of other blood vessels in the mucous membrane, the depth range Ad, and the like. Note that the factor α and the factor β differ depending on the structure of interest, that is, the selected illumination light.

In a case of the special observation mode, the display control unit 66 sequentially acquires the above structure-of-interest emphasized image from the image generating unit 77 and sequentially converts the structure-of-interest emphasized image into an image in a format suitable for display on the monitor 18 and outputs the image. Thus, in the case of the special observation mode, a physician or the like can observe the observation target by using a motion picture of the structure-of-interest emphasized image.

Figure 7:
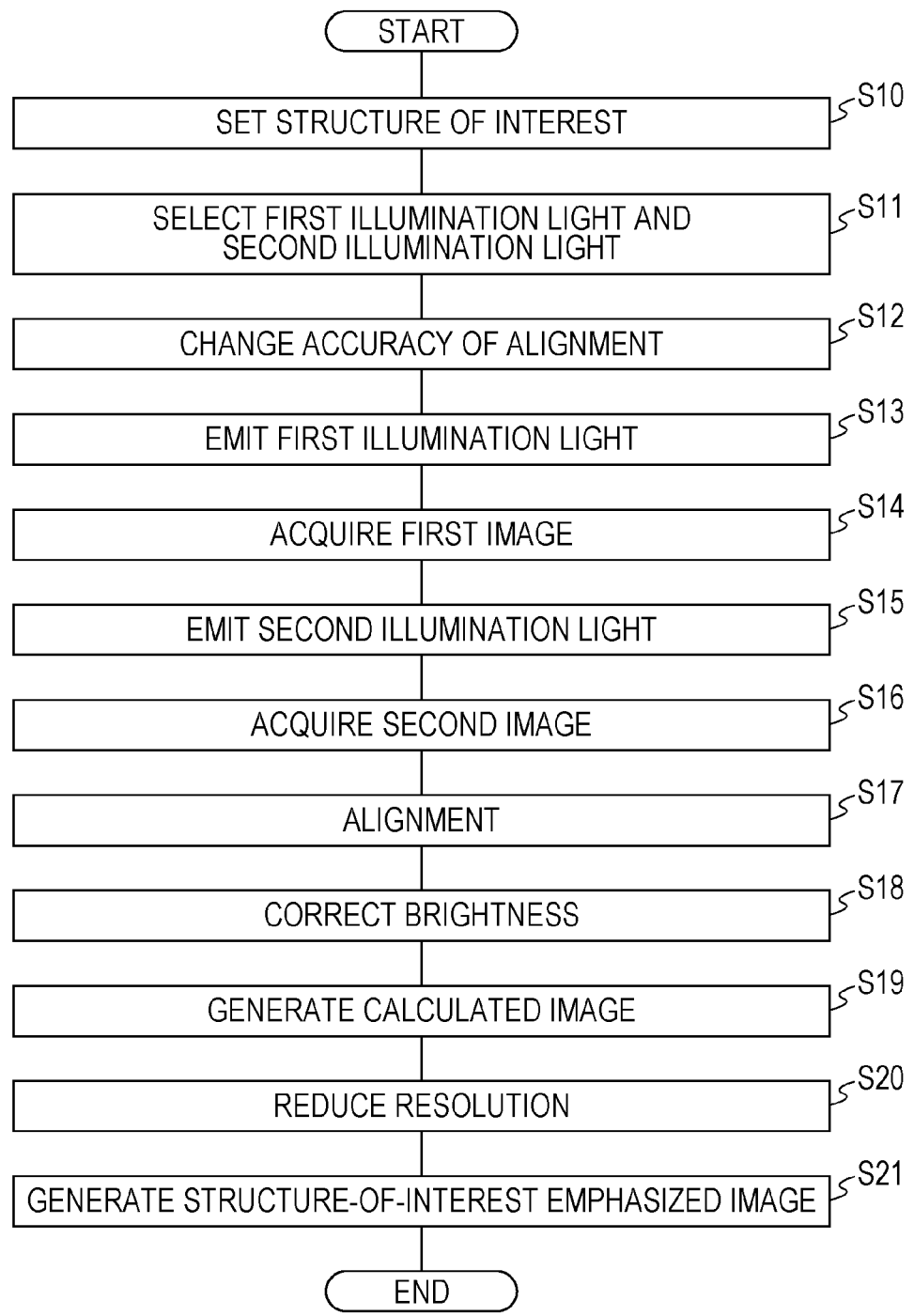
FIG. 7 is a flowchart illustrating an operation flow in a special observation mode.

Next, a flow of image processing performed by the endoscope system 10 in the special observation mode will be described with reference to FIG. 7. First, by using the console 19 or the like, a physician or the like sets a structure of interest to be observed in a distinguished manner from other tissues and the like in the special observation mode (S10). Specifically, the structure of interest is set by, for example, setting and inputting the numerical value of the wavelength of the illumination light to be used in the special observation mode in accordance with the structure of interest. In the following description, as an example, the structure of interest is a most superficial blood vessel, and the wavelength of the first illumination light is set to 400 nm and the wavelength of the second illumination light is set to 450 nm in order to emphasize and observe the most superficial blood vessel.

In response to switching to the special observation mode in the state in which the structure of interest is set, or in response to the setting and inputting of the structure of interest following the switching to the special observation mode, in accordance with the setting of the structure of interest, the illumination light selecting unit 51 selects the first illumination light and the second illumination light to be used in the special observation mode (S11). For simplicity, if the endoscope system 10 is capable of selecting any of the violet light V, the blue light B, the green light G, and the red light R as the first illumination light and the second illumination light, in accordance with the setting and inputting of the structure of interest, the illumination light selecting unit 51 selects the violet light V as the first illumination light and the blue light B as the second illumination light.

Upon the illumination light selecting unit 51 selecting the first illumination light and the second illumination light as described above, in accordance with the structure of interest, the accuracy changing unit 72 changes the accuracy of the alignment performed by the alignment unit 71 (S12). Specifically, the accuracy changing unit 72 changes the setting of the accuracy of the alignment to be higher as the violet light V serving as the first illumination light, the blue light B serving as the second illumination light, or the combination thereof has a shorter wavelength. Alternatively, in contrast, the accuracy changing unit 72 changes the setting of the accuracy of the alignment to be lower as the violet light V serving as the first illumination light, the blue light B serving as the second illumination light, or the combination thereof has a longer wavelength. Thus, as a result, the accuracy changing unit 72 sets the accuracy of the alignment suitable for emphasizing the most superficial blood vessel, which is the structure of interest.

Figure 8:
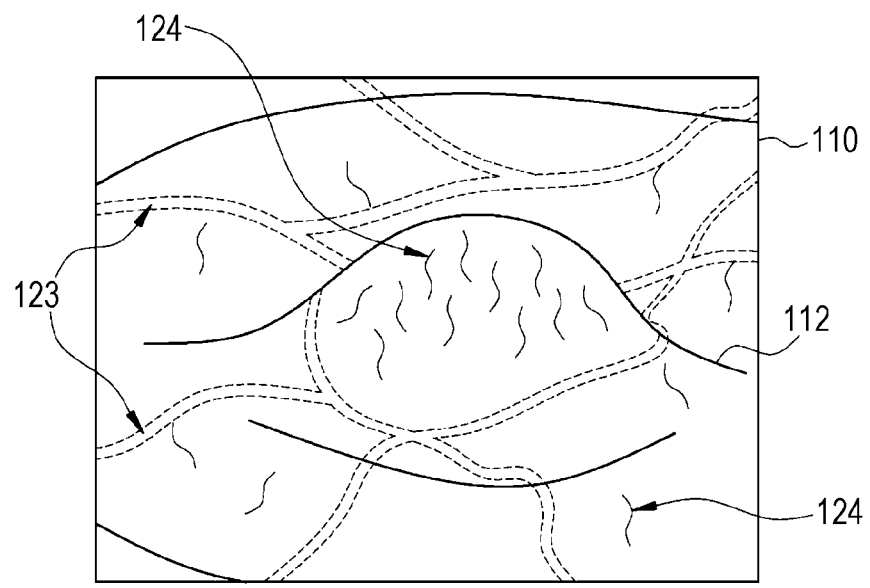
FIG. 8 is a schematic diagram of a V image.

On the other hand, upon the illumination light selecting unit 51 selecting the first illumination light and the second illumination light, the light source unit 20 first emits the violet light V, which is the first illumination light (S13). Then, the image sensor 48 images the observation target irradiated with the violet light V, and thereby the image acquiring unit 54 acquires a V image 110 that is the first image corresponding to the first illumination light (S14). As illustrated in FIG. 8, in the V image 110 obtained in this step, in addition to a shape 112 such as a slope in the observation target, a most superficial blood vessel 124 is observable. In addition, a superficial blood vessel 123 at a deeper position than the most superficial blood vessel 124 under the mucous membrane is also observable by using the V image 110.

Figure 9:
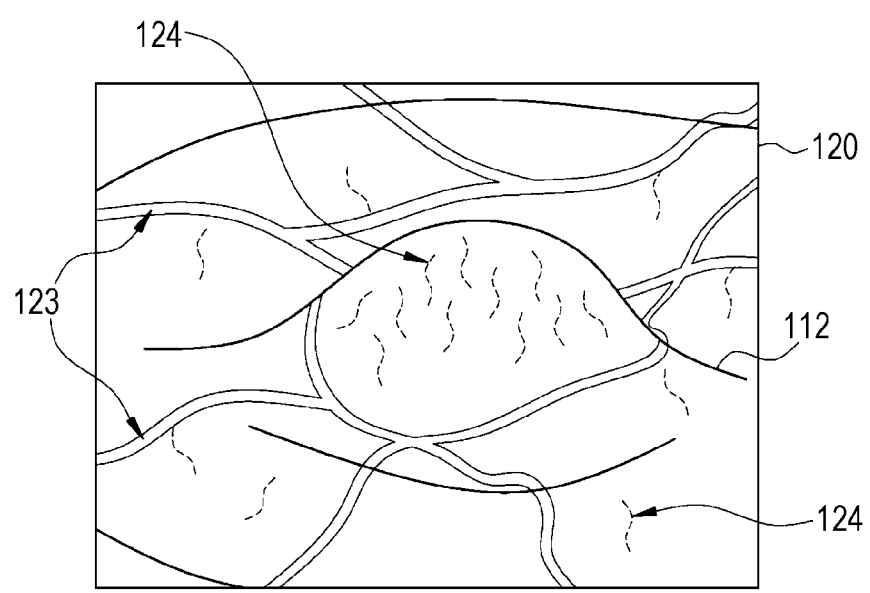
FIG. 9 is a schematic diagram of a B image.

Upon the V image 110 being acquired in this manner, the light source unit 20 emits the blue light B, which is the second illumination light (S15). The image sensor 48 images the observation target irradiated with the blue light B, and thereby the image acquiring unit 54 acquires a B image 120 that is the second image corresponding to the second illumination light (S16). As illustrated in FIG. 9, in the B image 120, in addition to the shape 112 of the observation target, the superficial blood vessel 123 at a relatively deep position is observable. In addition, the most superficial blood vessel 124 is also observable by using the B image 120. Note that if the V image 110 is compared with the B image 120, the contrast of the most superficial blood vessel 124 is higher in the V image 110, and the contrast of the superficial blood vessel 123 at a deeper position than the most superficial blood vessel 124 is higher in the B image 120.

Upon the image acquiring unit 54 acquiring the V image 110 and the B image 120 as described above, the alignment unit 71 aligns the V image 110, which is the first image, and the B image 120, which is the second image (S17). The alignment unit 71 aligns the V image 110 and the B image 120 at the accuracy that is changed and set by the accuracy changing unit 72 in step S12. That is, the alignment unit 71 does not constantly perform alignment at a high accuracy, but performs alignment within a minimum period of time in accordance with the type of structure of interest, and completes the alignment immediately.

Figure 10:
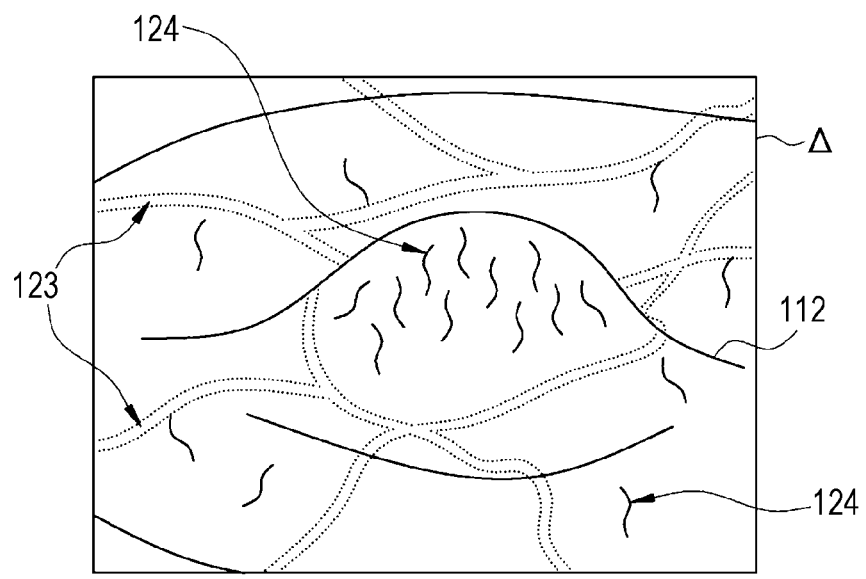
FIG. 10 is a schematic diagram of a calculated image.

Upon completion of the alignment, the brightness correcting unit 73 corrects the brightness of the V image 110, which is the first image, and the B image 120, which is the second image (S18), and the calculated image generating unit 74 subtracts the B image 120, which is the second image, from the V image 110, which is the first image, to generate the calculated image Δ (S19). In the calculated image Δ, compared to the original V image 110 and the B image 120, the superficial blood vessel 123 at a relatively deep position under the mucous membrane has a smaller pixel value, and the most superficial blood vessel 124 has a larger pixel value. Thus, as illustrated in FIG. 10, in the calculated image Δ, the difference between the most superficial blood vessel 124 and the superficial blood vessel 123 at a relatively deep position under the mucous membrane becomes clearer than in the V image 110.

Figure 11:
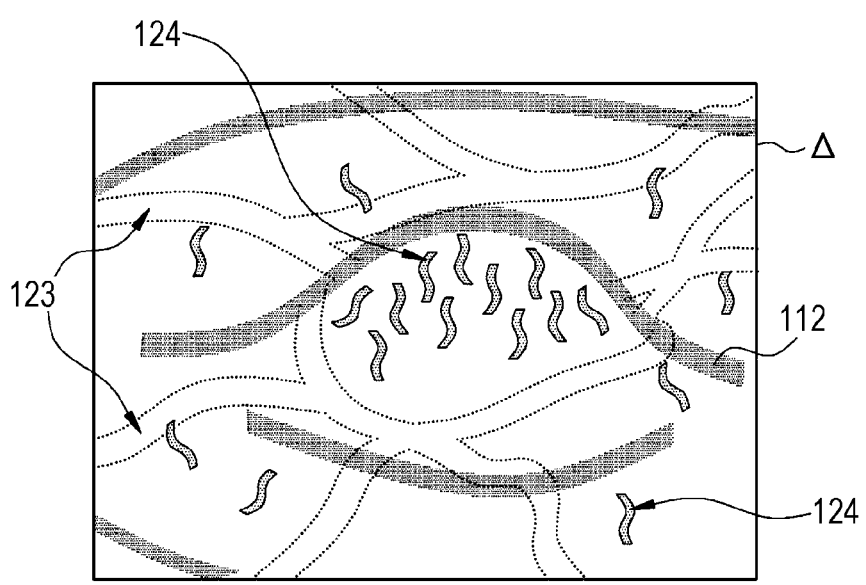
FIG. 11 is a schematic diagram of a calculated image with a reduced resolution.

The resolution of the calculated image Δ generated by the calculated image generating unit 74 is reduced by the resolution reducing unit 76 (S20). As illustrated in FIG. 11, in the calculated image Δ having a reduced resolution, the most superficial blood vessel 124 and the superficial blood vessel 123 blur.

Figure 12:
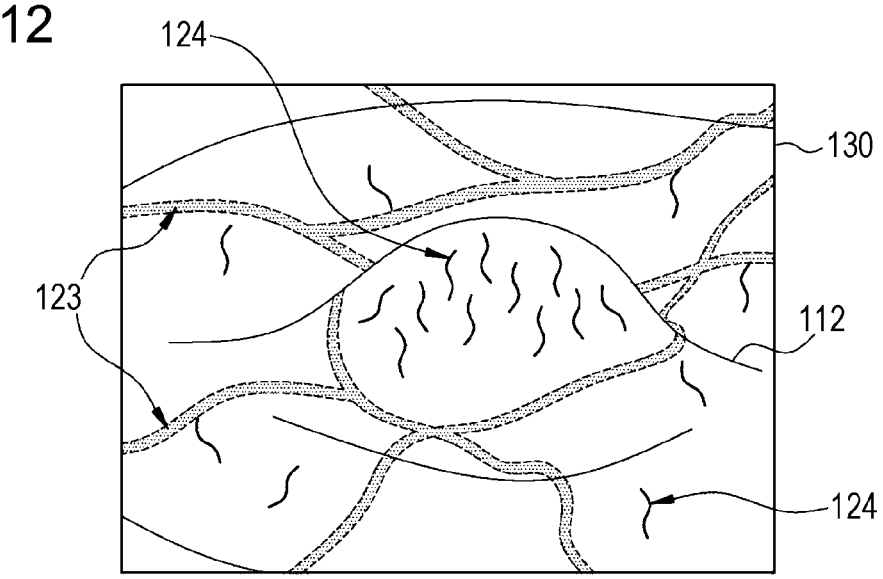
FIG. 12 is a schematic diagram of a structure-of-interest emphasized image.

Subsequently, the image generating unit 77 assigns the V image 110, which is the first image, to the luminance channel Y and the calculated image Δ with a reduced resolution to the chroma channels Cb and Cr, thereby generating a structure-of-interest emphasized image 130 (S21). As illustrated in FIG. 12, in the structure-of-interest emphasized image 130, the superficial blood vessel 123 at a relatively deep position is colored in a cyan-based color, and the most superficial blood vessel 124 is colored in a magenta-based color. Thus, the structure-of-interest emphasized image 130 emphasizes the most superficial blood vessel 124, which is the structure of interest, by using a color that is different from that of the superficial blood vessel 123 at a relatively deep position, so that the most superficial blood vessel 124, which is the structure of interest, is easily identified.

Unless the setting of the structure of interest is changed, the endoscope system 10 repeats the above operation of step S13 through step S21. Thus, the display control unit 66 sequentially acquires the structure-of-interest emphasized image 130 that is generated in the above manner and displays the structure-of-interest emphasized image 130 on the monitor 18. Accordingly, in the special observation mode, a physician or the like can observe a motion picture of the structure-of-interest emphasized image 130. Once the setting of the structure of interest is changed, the process is performed again from step S10.

In the above manner, in the special observation mode, the endoscope system 10 aligns the first image and the second image that are obtained by imaging the observation target at different timings by using the first illumination light and the second illumination light. The first image and the second image are aligned in this manner in order to emphasize the structure of interest accurately. Accordingly, if it is the only object to emphasize the structure of interest accurately, it is desirable that the first image and the second image be aligned at an accuracy as high as possible. However, the alignment involves a heavy processing load and takes time, and thus, the frame rate of a motion picture displayed on the monitor 18 for the alignment is decreased as the accuracy is increased. From the above, in the endoscope system 10, the first image and the second image are not simply aligned at a high accuracy, but the accuracy changing unit 72 appropriately changes the accuracy of the alignment as described above. This enables the endoscope system 10 to maintain the frame rate of the motion picture displayed on the monitor 18 as high as possible and enables the first image and the second image to be aligned at a necessary and sufficient accuracy.

Note that although the accuracy of the alignment is changed linearly (FIG. 4) in accordance with the length of the wavelength of the selected illumination light selected by the illumination light selecting unit 51 in the above first embodiment, in accordance with the wavelength of the selected illumination light, the accuracy of the alignment may be changed in accordance with a function that changes in curve or a monotone function. Alternatively, the accuracy of the alignment may be changed stepwise in accordance with the wavelength of the selected illumination light.

Second Embodiment

Although the wavelength and the like of the first illumination light and the second illumination light to be used in the special observation mode are set and input to allow the illumination light selecting unit 51 to select appropriate illumination light in the above first embodiment, instead, information on the depth and the like of a structure of interest may be set and input to allow the illumination light selecting unit 51 to select the first illumination light and the second illumination light by using the information on the depth and the like of the structure of interest.

Figure 13:
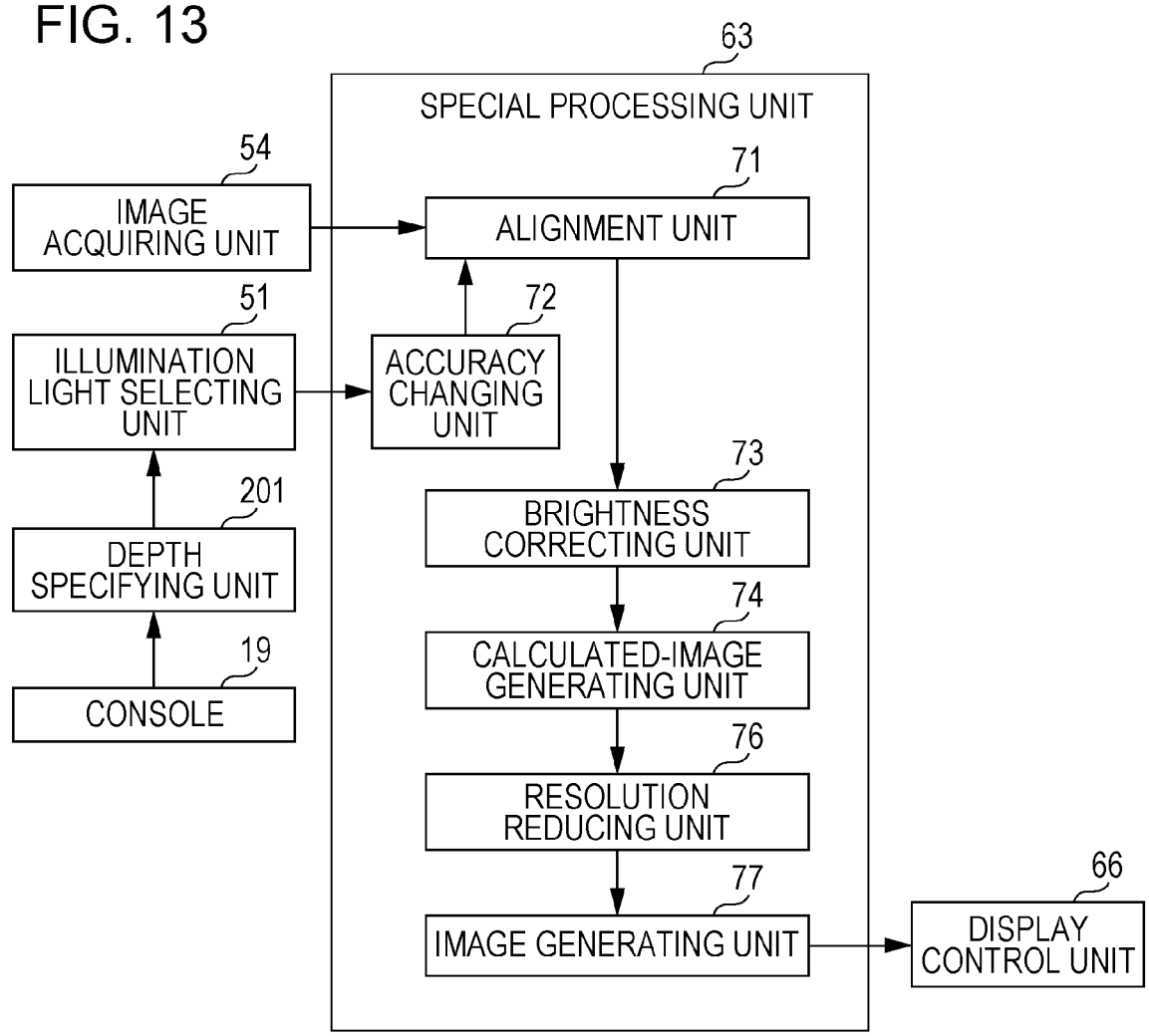
FIG. 13 is a block diagram illustrating a relationship between a depth specifying unit and a special processing unit.

In this case, as illustrated in FIG. 13, a depth specifying unit 201 is provided in the processor device 16. Upon reception of an input operation on the console 19 or the like, the depth specifying unit 201 specifies the depth of the structure of interest under the mucous membrane and transmits the depth to the illumination light selecting unit 51. For example, a numeric value or a range of numeric values of a distance (depth) from a mucosal surface or the like as a reference is input. The depth of the structure of interest can also be specified in a simplified manner by selection of a menu including predetermined information on depth, such as "most superficial blood vessel", "superficial blood vessel, "middle-layer blood vessel", or "deep-layer blood vessel".

By using the depth specified by the depth specifying unit 201, the illumination light selecting unit 51 specifies the first illumination light and the second illumination light. For example, in a case in which the structure of interest is the most superficial blood vessel 124, in response to the numerical value of the depth of the most superficial blood vessel 124 being input or a "most superficial blood vessel" menu being selected, the depth specifying unit 201 specifies the depth and transmits the depth to the illumination light selecting unit 51, and thus, the illumination light selecting unit 51 selects the violet light V as the first illumination light and the blue light B as the second illumination light.

If the special observation mode is operated in accordance with the specification of the depth of the structure of interest as described above, a physician or the like does not have to consider the wavelengths and the like of the first illumination light and the second illumination light to appropriately observe the structure of interest, and accordingly, the special observation mode can be used more easily.

Figure 14:
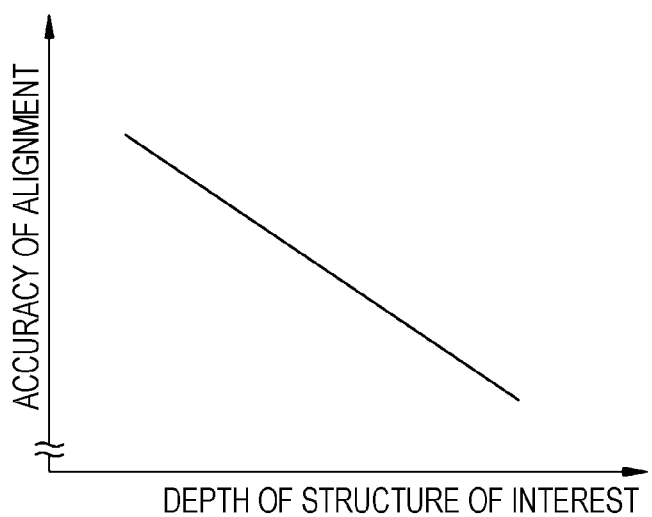
FIG. 14 is a graph illustrating a relationship between the depth of a structure of interest and the accuracy of alignment.

As in the first embodiment, the accuracy changing unit 72 changes the accuracy of the alignment performed by the alignment unit 71 in accordance with the selected illumination light selected by the illumination light selecting unit 51. However, in a case in which the depth specifying unit 201 is provided as described above, instead of the selected illumination light, by using the information on the depth specified by the depth specifying unit 201, the accuracy changing unit 72 can change the accuracy of the alignment performed by the alignment unit 71. In this case, as illustrated in FIG. 14, the accuracy changing unit 72 increases the accuracy of the alignment as the depth of the structure of interest specified by the depth specifying unit 201 is shallower, and decreases the accuracy of the alignment as the depth of the structure of interest specified by the depth specifying unit 201 is deeper. This substantially equals to increasing the accuracy of the alignment as the selected illumination light has a shorter wavelength and decreasing the accuracy of the alignment as the selected illumination light has a longer wavelength.

In addition, in a case in which the depth specifying unit 201 is provided as described above, by using the selected illumination light selected by the illumination light selecting unit 51 and the depth specified by the depth specifying unit 201, the accuracy of the alignment performed by the alignment unit 71 can be changed. Also in this case, as in the above first embodiment and the second embodiment, the accuracy of the alignment is increased as the selected illumination light has a shorter wavelength, and the accuracy of the alignment is decreased as the selected illumination light has a longer wavelength. In addition, the accuracy of the alignment is increased as the specified depth is shallower, and the accuracy of the alignment is decreased as the specified depth is deeper. By changing the accuracy of the alignment in accordance with the selected illumination light and the depth specified by the depth specifying unit 201 in this manner, the setting of the accuracy of the alignment can be changed more appropriately than in the above first embodiment and the second embodiment.

Although the accuracy of the alignment is changed linearly by using the specified depth of the structure of interest in the above second embodiment (FIG. 14), the accuracy of the alignment may be changed in accordance with a function that changes in curve or a monotone function by using the specified depth of the structure of interest. Besides, the accuracy of the alignment can be changed stepwise by using the specified depth of the structure of interest. In addition, although the depth specifying unit 201 is provided in the processor device 16 in the above second embodiment, the depth specifying unit 201 may be incorporated in the special processing unit 63.

Third Embodiment

Although the accuracy changing unit 72 in the first embodiment and the second embodiment changes the accuracy of the alignment performed by the alignment unit 71 by using the selected illumination light selected by the illumination light selecting unit 51 and the depth of the structure of interest specified by the depth specifying unit 201, the accuracy changing unit 72 can change the accuracy of the alignment performed by the alignment unit 71 by using, instead of any of the above parameters, the degree of movement (hereinafter referred to as a movement amount) of the observation target between the first image and the second image.

Figure 15:
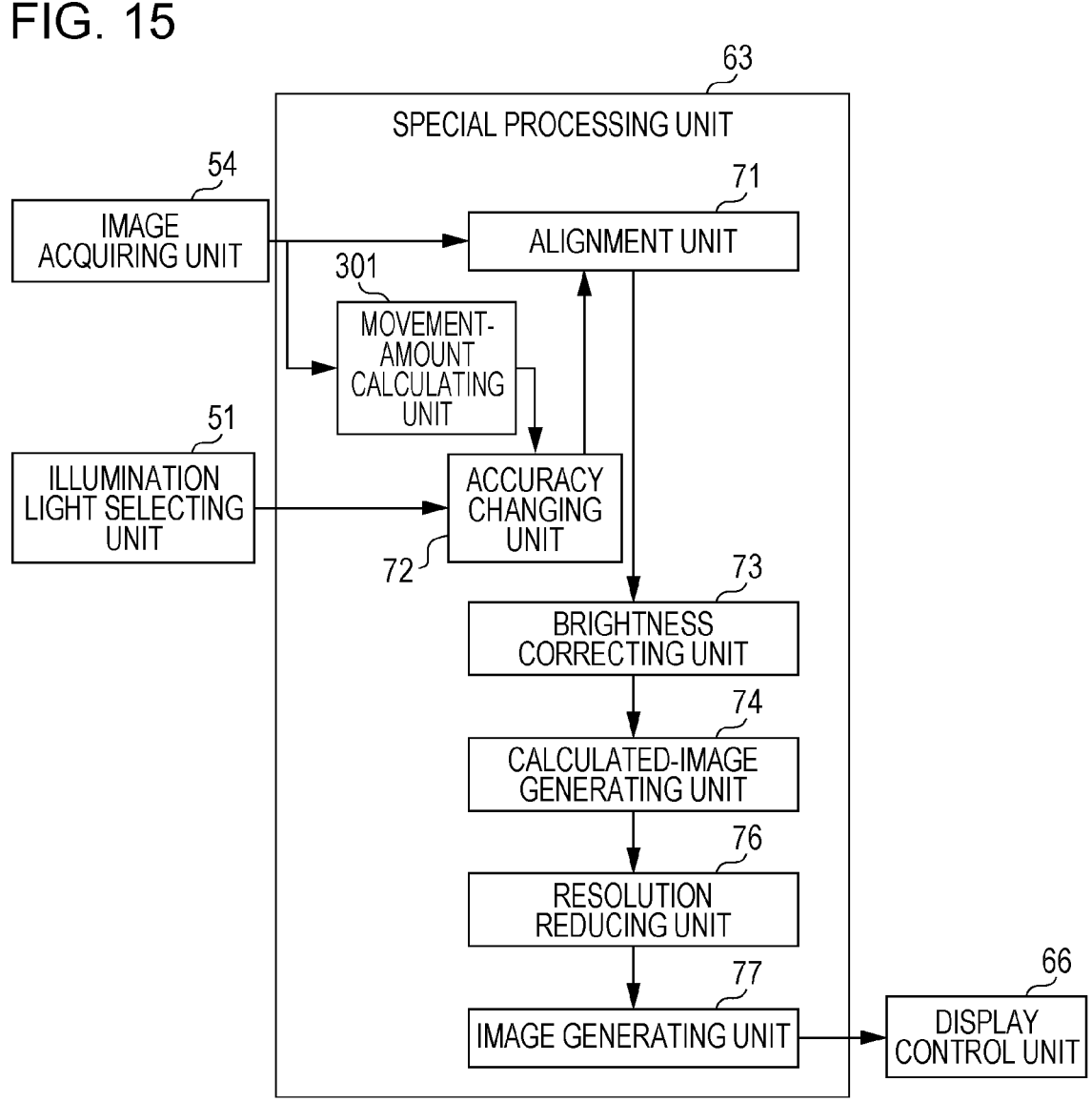
FIG. 15 is a block diagram of a special processing unit provided with a movement-amount calculating unit.

In this case, as illustrated in FIG. 15, the special processing unit 63 is provided with a movement-amount calculating unit 301. The movement-amount calculating unit 301 acquires the first image and the second image from the image acquiring unit 54 and calculates the movement amount of the observation target therebetween. Specifically, the movement-amount calculating unit 301 obtains a motion vector between the observation target in the first image and the observation target in the second image by performing matching between the first image and the second image, calculates a statistic (average, median, maximum, or the like) of the level of the motion vector, and sets the statistic as the movement amount.

As in the first embodiment, the accuracy changing unit 72 changes the accuracy of the alignment performed by the alignment unit 71 in accordance with the selected illumination light selected by the illumination light selecting unit 51. However, in this embodiment, the accuracy of the alignment performed by the alignment unit 71 is changed by further using the movement amount calculated by the movement-amount calculating unit 301. Specifically, the accuracy changing unit 72 increases the accuracy of the alignment as the selected illumination light has a shorter wavelength and decreases the accuracy of the alignment as the selected illumination light has a longer wavelength, and increases the accuracy of the alignment as the movement amount is smaller and decreases the accuracy of the alignment as the movement amount is larger. When cases in which the wavelengths of the selected illumination light are, for convenience, $\lambda 1$, $\lambda 2$, and $\lambda 3$ ($\lambda 3 > \lambda 2 > \lambda 1$) are compared with one another, for example, the accuracy changing unit 72 changes the accuracy of the alignment in accordance with the graph illustrated in FIG. 16. That is, according to the wavelength of the selected illumination light, the accuracy of the alignment is increased as the movement amount is smaller, and the accuracy of the alignment is decreased as the movement amount is larger. This is because, if the movement amount is large, an artifact, if any, as a result of a low accuracy of the alignment is unlikely to be noticed in a motion picture displayed on the monitor 18, and the alignment at a high accuracy produces substantially no effects.

If the movement amount is further taken into account as described above, the setting of the accuracy of the alignment can be changed to a more appropriate value, and it is likely to align the first image and the second image at a necessary and sufficient accuracy while maintaining the frame rate of the motion picture displayed on the monitor 18.

The third embodiment can be combined with not only the first embodiment but also the second embodiment. The third embodiment can also be combined with both the first embodiment and the second embodiment. In a case in which the depth specifying unit 201 is provided as in the second embodiment, the accuracy of the alignment is increased as the depth of the structure of interest specified by the depth specifying unit 201 is shallower, and the accuracy of the alignment is decreased as the depth of the structure of interest specified by the depth specifying unit 201 is deeper. In addition, the accuracy of the alignment is increased as the movement amount is smaller, and the accuracy of the alignment is decreased as the movement amount is larger.

Figure 16:
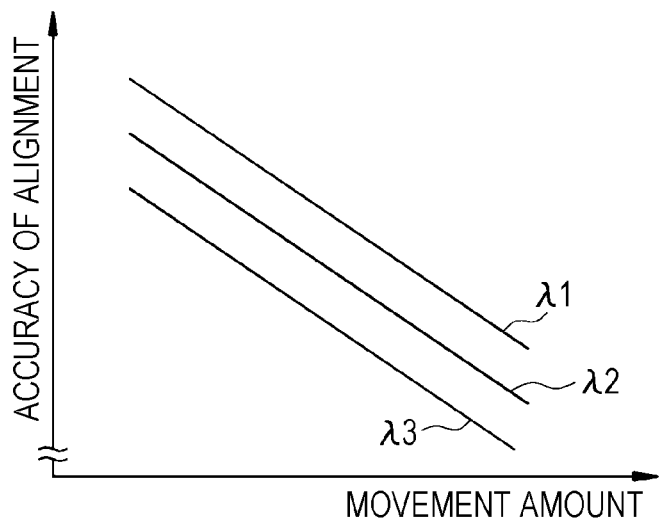
FIG. 16 is a graph illustrating a relationship between a movement amount and the accuracy of alignment.
Figure 17:
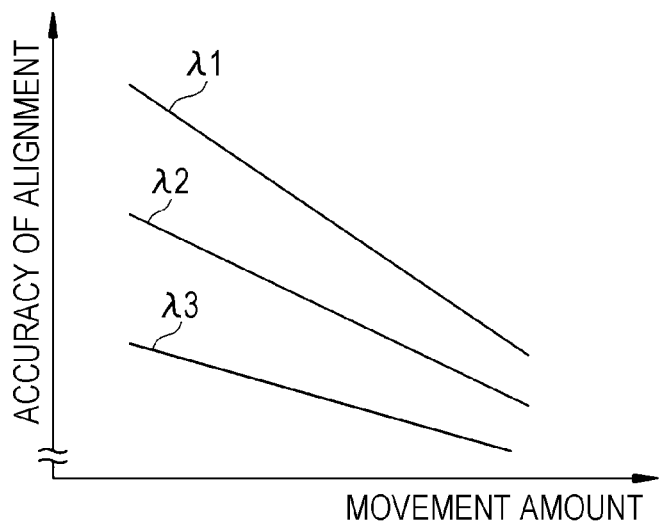
FIG. 17 is a graph illustrating a relationship between the movement amount and the accuracy of alignment.
Figure 18:
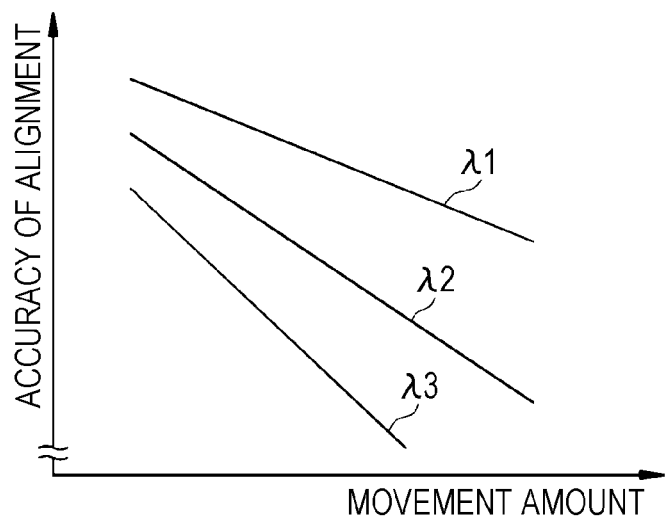
FIG. 18 is a graph illustrating a relationship between the movement amount and the accuracy of alignment.

The graphs of $\lambda 1$, $\lambda 2$, and $\lambda 3$ are substantially parallel with one another in FIG. 16, and the accuracy of the alignment is uniquely changed by using the movement amount regardless of the wavelengths of the selected illumination light selected by the illumination light selecting unit 51. However, for example, as illustrated in FIGS. 17 and 18, the changing ratio of the accuracy of the alignment in accordance with the movement amount may be changed depending on the wavelength of the selected illumination light. This technique is similarly applicable to a case in which the depth specifying unit 201 according to the second embodiment is combined.

Although the accuracy of the alignment is changed linearly by using the movement amount in the above third embodiment (FIGS. 16 to 18), the accuracy of the alignment may be changed in accordance with a function that changes in curve or a monotone function by using the movement amount. Besides, the accuracy of the alignment may be changed stepwise by using the movement amount. This technique is similarly applicable to a case in which the depth specifying unit 201 according to the second embodiment is combined.

Figure 19:
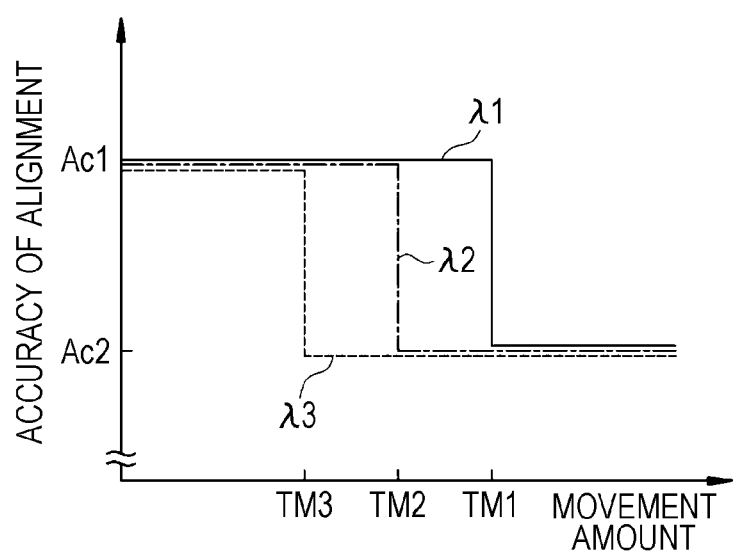
FIG. 19 is a graph illustrating a relationship between the movement amount and the accuracy of alignment.

In a case in which the accuracy of the alignment is changed stepwise by using the movement amount, for example, as illustrated in FIG. 19, with $\lambda 1$ having the shortest wavelength as the wavelength of the selected illumination light, in response to the movement amount becoming equal to or smaller than a movement amount threshold TM1, the accuracy of the alignment is changed from Ac2 to Ac1 (Ac1>Ac2). With λ2 having a longer wavelength than λ1 as the wavelength of the selected illumination light, in response to the movement amount becoming equal to or smaller than a smaller movement amount threshold TM2 (<TM1), the accuracy of the alignment is changed from Ac2 to Ac1. Similarly, with λ3 having an even longer wavelength than λ2 as the wavelength of the selected illumination light, in response to the movement amount becoming equal to or smaller than an even smaller movement amount threshold TM3 (<TM2), the accuracy of the alignment is changed from Ac2 to Ac1 . In the above manner, in a case in which the accuracy of the alignment is changed stepwise by using the movement amount, the movement amount threshold for changing the accuracy of the alignment is larger as the wavelength of the selected illumination light is shorter. This is because, as the wavelength of the selected illumination light is shorter, the structure of interest is finer and shallower, and accordingly, influence of an artifact as a result of a low accuracy of the alignment is relatively large.

The accuracy of the alignment is changed in two steps, Ac1 and Ac2, in FIG. 19, but this technique is similarly applicable to a case in which the accuracy of the alignment is changed in three or more steps. In addition, the accuracy of the alignment to be changed stepwise is the same regardless of the wavelength of the selected illumination light in FIG. 19, but the accuracy of the alignment to be changed stepwise can be changed according to the wavelength of the selected illumination light. This technique is similarly applicable to a case in which the depth specifying unit 201 according to the second embodiment is combined.

Fourth Embodiment

In the above third embodiment, the accuracy changing unit 72 changes the accuracy of the alignment performed by the alignment unit 71 in accordance with the movement amount, that is, the relative degree of movement of the observation target between the first image and the second image. However, the accuracy changing unit 72 preferably changes the accuracy of the alignment performed by the alignment unit 71 in accordance with the degree of movement of the observation target in the first image, the degree of movement of the observation target in the second image, or both the degree of movement of the observation target in the first image and the degree of movement of the observation target in the second image. The movement of the observation target in the first image (or the second image) is the movement of the observation target when imaging the first image (or the second image) or a relative movement between the observation target and the endoscope 12. Accordingly, the degree of movement of the observation target in the first image (or the second image) is a so-called degree of blur (hereinafter referred to as a blur amount) in the first image (or the second image).

Figure 20:
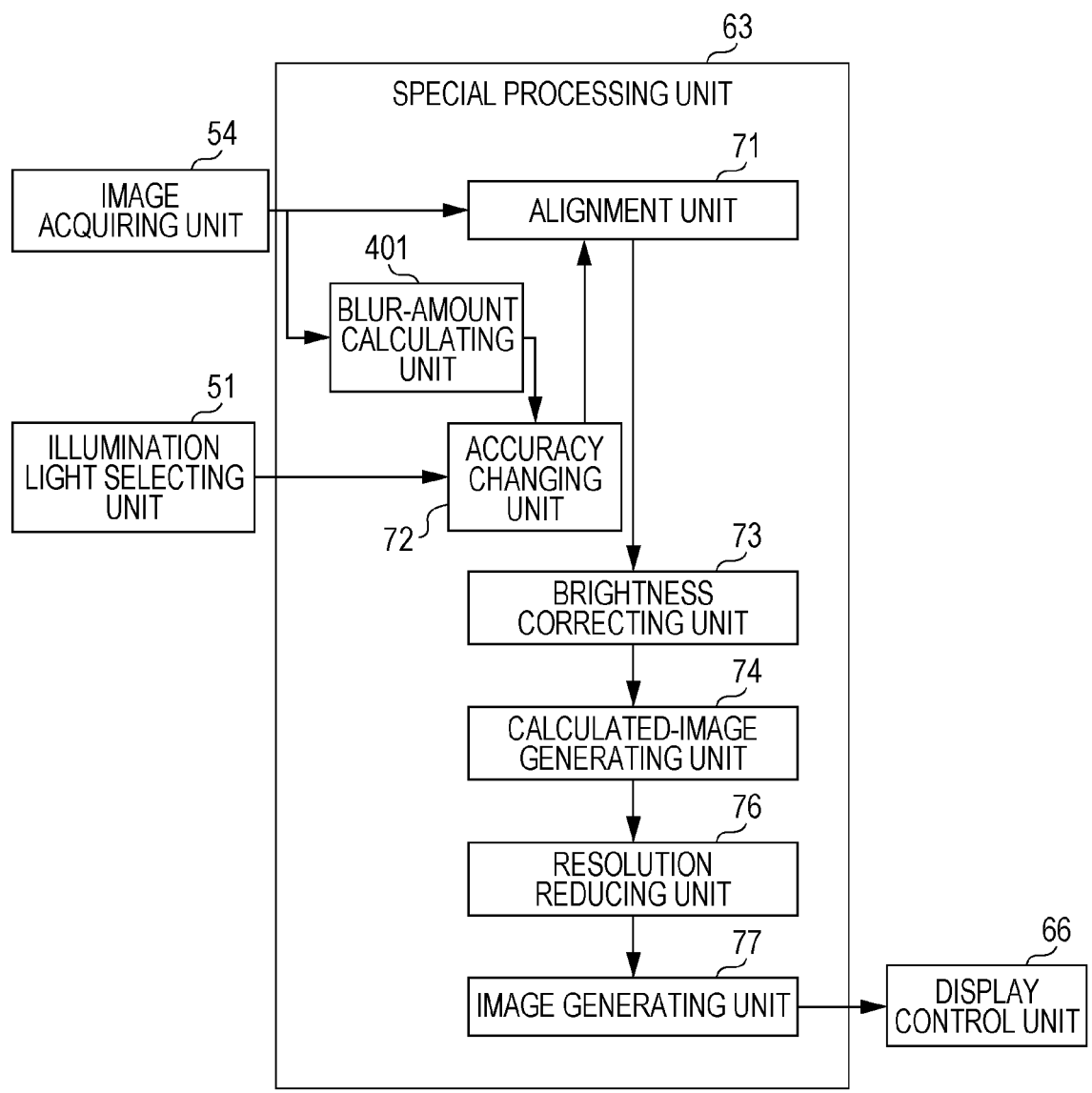
FIG. 20 is a block diagram of a special processing unit provided with a blur-amount calculating unit.

In a case in which the accuracy changing unit 72 changes the accuracy of the alignment performed by the alignment unit 71 by using the blur amount in the first image, the blur amount in the second image, or the blur amounts in both the first image and the second image, as illustrated in FIG. 20, for example, the special processing unit 63 is provided with a blur-amount calculating unit 401 for calculating the blur amount. The blur-amount calculating unit 401, for example, calculates the blur amount through frequency analysis. More specifically, a spectrum is obtained by Fourier transformation of the first image (or the second image), and an intensity ratio between a low-frequency component and a high-frequency component is calculated, and the blur amount of the first image (or the second image) is calculated. If the low-frequency component is large or the high-frequency component is small, the blur amount is large; if the low-frequency component is small or the high-frequency component is large, the blur amount is small.

As in the first embodiment, the accuracy changing unit 72 changes the accuracy of the alignment performed by the alignment unit 71 in accordance with the selected illumination light selected by the illumination light selecting unit 51. However, in this embodiment, the accuracy of the alignment performed by the alignment unit 71 is changed by further using the blur amount calculated by the blur-amount calculating unit 401.

Figure 21:
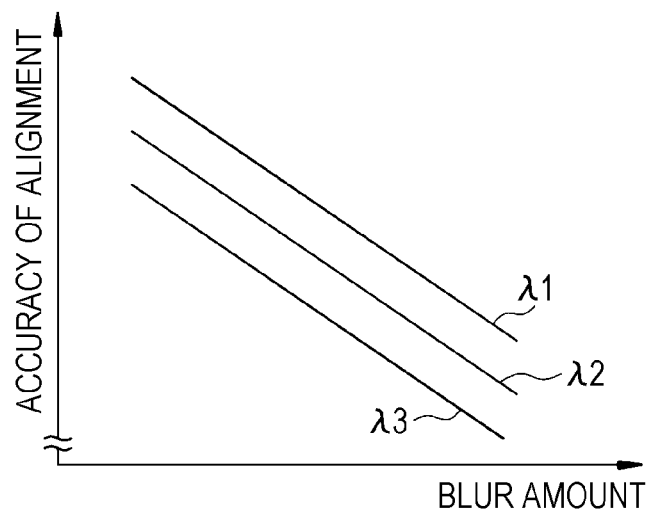
FIG. 21 is a graph illustrating a relationship between a blur amount and the accuracy of alignment.

In order to change the accuracy of the alignment by using the blur amount, the accuracy changing unit 72 compares the blur amount calculated by the blur-amount calculating unit 401 with a threshold that is set in advance. Specifically, the accuracy changing unit 72 increases the accuracy of the alignment as the blur amount is smaller and decreases the accuracy of the alignment as the blur amount is larger. When cases in which the wavelengths of the selected illumination light are, for convenience, λ1, λ2, and λ3 (λ3>λ2>λ1) are compared with one another, for example, the accuracy changing unit 72 changes the accuracy of the alignment in accordance with the graph illustrated in FIG. 21. That is, the accuracy of the alignment is changed by using the blur amount in the same manner as that in a case in which the accuracy of the alignment is changed by using the movement amount (the third embodiment, see FIG. 16). As in a modification example (FIG. 17 or FIG. 18) of the third embodiment, the accuracy changing unit 72 according to this embodiment may change the changing ratio of the accuracy of the alignment by using the blur amount according to the wavelength of the selected illumination light. In addition, as in another modification example (FIG. 19) of the third embodiment, the accuracy changing unit 72 according to this embodiment can change the accuracy of the alignment stepwise by using the blur amount.

Note that in a case in which the accuracy of the alignment is changed by using the blur amount, the accuracy changing unit 72 preferably causes the alignment unit 71 to perform the alignment or prevents the alignment unit 71 from performing the alignment by using the blur amount. Specifically, if the blur amount is larger than the threshold, the accuracy changing unit 72 prevents the alignment unit 71 from performing the alignment of the first image and the second image. Thus, the alignment unit 71 skips the alignment. If the blur amount is smaller than or equal to the threshold, the accuracy changing unit 72 causes the alignment unit 71 to perform the alignment, and as in the first embodiment, the accuracy changing unit 72 increases the accuracy of the alignment as the selected illumination light has a shorter wavelength and decreases the accuracy of the alignment as the selected illumination light has a longer wavelength. In this case, the alignment unit 71 aligns the first image and the second image at an accuracy that is changed and set by the accuracy changing unit 72.

If the blur amount is too large with respect to the frame rate of a motion picture displayed on the monitor 18, even if one frame of image therein is visually recognized as a still image, the structure of interest is unobservable regardless of the presence and absence of an artifact. Accordingly, even if an artifact is generated by skipping the alignment as a result of the large blur amount as in the above case, the observation is not influenced at all because the structure of interest is unobservable. Thus, if the blur amount is large as in the above case, the accuracy changing unit 72 prioritizes the frame rate of a motion picture displayed on the monitor 18 and skips the alignment.

Figure 22:
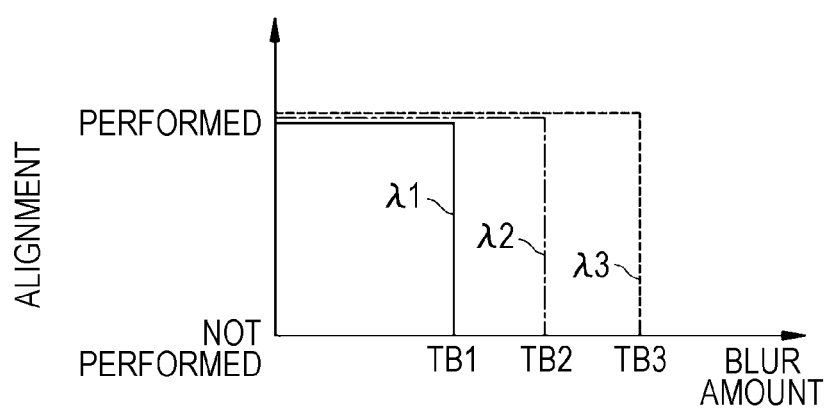
FIG. 22 is a graph illustrating a relationship between the blur amount and alignment or the absence of alignment.

When cases in which the wavelengths of the selected illumination light are, for convenience, $\lambda 1$, $\lambda 2$, and $\lambda 3$ ($\lambda 3 > \lambda 2 > \lambda 1$) are compared with one another, for example, the accuracy changing unit 72 causes the alignment to be performed or prevents the alignment from being performed in accordance with the graph illustrated in FIG. 22. That is, with the shortest wavelength $\lambda 1$ as the wavelength of the selected illumination light, a blur amount TB1 that is the smallest blur amount is set as the threshold. If the blur amount is smaller than or equal to the threshold TB1, the alignment is performed; if the blur amount is larger than the threshold TB1, the alignment is not performed. Next, with the short wavelength $\lambda 2$ as the wavelength of the selected illumination light, a blur amount TB2 that is larger than the threshold TB1 for the wavelength $\lambda 1$ (TB>TB1) is set as the threshold. If the blur amount is smaller than or equal to the threshold TB2, the alignment is performed; if the blur amount is larger than the threshold TB2, the alignment is not performed. Similarly, with the longest wavelength $\lambda 3$ as the wavelength of the selected illumination light, a blur amount TB3 that is larger than the threshold TB2 for the wavelength $\lambda 2$ (TB3>TB2) is set as the threshold. If the blur amount is smaller than or equal to the threshold TB3, the alignment is performed; if the blur amount is larger than the threshold TB3, the alignment is not performed.

In the above manner, the blur amount threshold used by the accuracy changing unit 72 to determine whether the alignment is to be performed is set to a small amount if the selected illumination light has a short wavelength. This is because, the shorter the wavelength of the selected illumination light, the smaller and finer the structure of interest, and accordingly, even a comparably small blur may make the structure of interest unobservable depending on the blur of the observation target in a motion picture displayed on the monitor 18.

The accuracy changing unit 72 can use the blur amount to determine a specific accuracy of the alignment and to determine whether the alignment is to be performed. Alternatively, the blur amount may be used only to determine whether the alignment is to be performed as in the above case.

The above fourth embodiment can be combined with not only the first embodiment but also the second embodiment and the third embodiment. Similarly, the modification example of the above fourth embodiment for determining whether the alignment is to be performed by using the blur amount can be combined with not only the first embodiment but also the second embodiment and the third embodiment. Note that, as in the fourth embodiment and the modification example thereof, the blur amount can be used to determine a specific accuracy of the alignment and to determine whether the alignment is to be performed. However, in a case in which the modification example of the fourth embodiment is combined with any of the first to third embodiments, the blur amount can only be used to determine whether the alignment is to be performed.

For example, in a case in which the depth specifying unit 201 according to the second embodiment is provided and in which the blur amount is used to determine whether the alignment is to be performed, the blur amount threshold for determining whether the alignment is to be performed can be switched by using the depth of the structure of interest specified by the depth specifying unit 201. Specifically, a smaller threshold for determining whether the alignment is to be performed may be set as the depth of the structure of interest specified by the depth specifying unit 201 is shallower, and a larger threshold for determining whether the alignment is to be performed may be set as the depth of the structure of interest specified by the depth specifying unit 201 is deeper. If the determination, by using the blur amount, as to whether the alignment is to be performed is combined with the first embodiment and the second embodiment, with the selection illumination light having a short wavelength, the blur amount threshold for determining whether the alignment is to be performed may be a small threshold, and in addition, the threshold for determining whether the alignment is to be performed may be a smaller threshold as the depth of the structure of interest specified by the depth specifying unit 201 is shallower.

Figure 23:
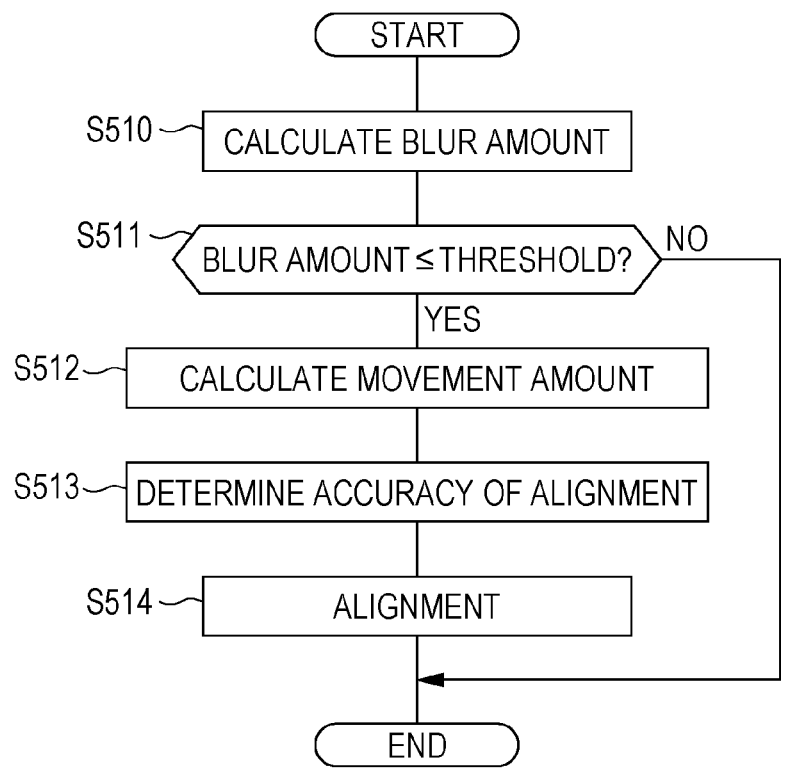
FIG. 23 is a flowchart in a case in which calculation of the blur amount is combined with calculation of the movement amount.

In a case in which the movement-amount calculating unit 301 according to the third embodiment is provided and in which the blur amount is used to determine whether the alignment is to be performed, as illustrated in FIG. 23, the blur-amount calculating unit 401 first calculates the blur amount (S510), and the accuracy changing unit 72 compares the blur amount with the threshold for determining whether the alignment is to be performed (S511). If the blur amount is smaller than or equal to the threshold (YES in S511), the movement-amount calculating unit 301 calculates the movement amount (S512), and on the basis of the movement amount and the like, the accuracy changing unit 72 determines the accuracy of the alignment (S513). Subsequently, the alignment unit 71 aligns the first image and the second image at the accuracy determined by the accuracy changing unit 72. On the other hand, if the blur amount is larger than the threshold (NO in S511), the calculation of the movement amount and the like is skipped. Before the first image and the second image are aligned, it is determined whether the alignment is to be performed. If the alignment is not to be performed, the alignment is not performed, and also, the calculation of the movement amount and the like is skipped as described above. In this case, a useless calculation can be omitted, and it is likely to maintain the frame rate of a motion picture displayed on the monitor 18.

Although the structure-of-interest emphasized image 130 in which the structure of interest is emphasized is generated and displayed in the above first to fourth embodiments, the present invention is suitably used in, in addition to a case in which the structure of interest is emphasized, a case in which the structure of interest is extracted and a case in which biological function information (oxygen saturation and the like) regarding the structure of interest is calculated. That is, the present invention is suitably used in a case in which calculation is performed by using the first image and the second image, which are obtained by imaging the observation target at different timings.

Figure 24:
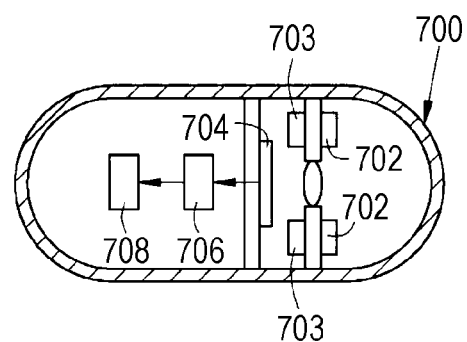
FIG. 24 is a schematic diagram of a capsule endoscope.

Although the present invention is implemented in the endoscope system that enables observation by inserting the endoscope 12 provided with the image sensor 48 into a subject in the above first to fourth embodiments, the present invention is also suitably used for a capsule endoscope system. As illustrated in FIG. 24, for example, the capsule endoscope system has at least a capsule endoscope 700 and a processor device (not illustrated).

The capsule endoscope 700 includes a light source unit 702, a control unit 703, an image sensor 704, an image processing unit 706, and a transmission/reception antenna 708. The light source unit 702 corresponds to the light source unit 20. The control unit 703 serves in substantially the same manner as the light source control unit 22 and the control unit 52. In addition, the control unit 703 can wirelessly communicate with the processor device of the capsule endoscope system by using the transmission/reception antenna 708. The processor device of the capsule endoscope system is substantially the same as the processor device 16 according to the above first to fourth embodiments, but the image processing unit 706 corresponding to the image acquiring unit 54 and the image processing unit 61 is provided in the capsule endoscope 700, and the structure-of-interest emphasized image 130 and the like that have been generated are transmitted to the processor device through the transmission/reception antenna 708. The image sensor 704 is configured in substantially the same manner as the image sensor 48.

REFERENCE SIGNS LIST 10 endoscope system
12 endoscope
12a insertion part
12b operating unit
12c bending part
12d tip part
12e angle knob
13a switch
13b zoom operating unit
14 light source device
16 processor device
18 monitor
19 console
20, 702 light source unit
20a V light source
20b B light source
20c G light source
20d R light source
22 light source control unit
30a illumination optical system
30b imaging optical system
41 light guide
45 illumination lens
46 objective lens
47 zoom lens
48, 704 image sensor
51 illumination light selecting unit
52, 703 control unit
54 image acquiring unit
56 DSP
58 noise reducing unit
59 conversion unit
61, 706 image processing unit
62 normal processing unit
63 special processing unit
66 display control unit
71 alignment unit
72 accuracy changing unit
73 brightness correcting unit
74 calculated image generating unit
76 resolution reducing unit
77 image generating unit
110 V image
112 shape
120 B image
123 superficial blood vessel
124 most superficial blood vessel
130 structure-of-interest emphasized image
201 depth specifying unit
301 movement-amount calculating unit
401 blur-amount calculating unit
700 capsule endoscope
708 transmission/reception antenna
Ad, As range
TM1, TM2, TM3, TB1, TB2, TB3 threshold

What is claimed is:

1. An endoscope system comprising a processor configured to:
    acquire a first image and a second image, the first image being obtained by imaging an observation target by using first illumination light, the second image being obtained by imaging the observation target by using second illumination light that is different from the first illumination light at a different timing from the first image;
    align the first mage and the second image; and
    change an accuracy of an alignment of the first image and the second image in accordance with at least a structure of interest to be observed,
    wherein the processor selects the first illumination light and the second illumination light for imaging the observation target in accordance with the structure of interest, and changes the accuracy of the alignment in accordance with the first illumination light, the second illumination light, or a combination of the first illumination light and the second illumination light selected by the processor,
    wherein the processor increases the accuracy of the alignment as a wavelength of the first illumination light, a wavelength of the second illumination light, or an average of wavelengths of the combination of the first illumination light and the second illumination light selected by the processor decreases.

2. The endoscope system according to claim 1,
    wherein the processor further specifies a depth of the structure of interest, and
    changes the accuracy of the alignment by using the depth specified.

3. The endoscope system according to claim 2,
    wherein the processor increases the accuracy of the alignment as the depth of the structure of interest specified by the processor decreases.

4. The endoscope system according to claim 2,
    wherein the processor further calculates a movement amount of the observation target by using the first image and the second image, and
    changes the accuracy of the alignment by using the movement amount.

5. The endoscope system according to claim 1,
    wherein the processor further calculates a movement amount of the observation target by using the first image and the second image, and
    changes the accuracy of the alignment by using the movement amount.

6. The endoscope system according to claim 5,
    wherein the processor increases the accuracy of the alignment as the movement amount is decreased.

7. The endoscope system according to claim 6,
    wherein the processor calculates a blur amount of the first image or the second image, and
    changes the accuracy of the alignment by using the blur amount.

8. The endoscope system according to claim 1,
    wherein the processor calculates a blur amount of the first image or the second image, and
    changes the accuracy of the alignment by using the blur amount.

9. The endoscope system according to claim 8, wherein the processor increases the accuracy of the alignment as the blur amount is decreased.

10. A processor device of an endoscope system, comprising a processor configured to:
   acquire a first image and a second image, the first image being obtained by imaging an observation target by using first illumination light, the second image being obtained by imaging the observation target by using second illumination light that is different from the first illumination light at a different timing from the first image;
   align the first image and the second image; and
   change an accuracy of an alignment of the first image and the second image in accordance with at least a structure of interest to be observed,
   wherein the processor selects the first illumination light and the second illumination light for imaging the observation target in accordance with the structure of interest, and changes the accuracy of the alignment in accordance with the first illumination light, the second illumination light, or a combination of the first illumination light and the second illumination light selected by the processor,
   wherein the processor increases the accuracy of the alignment as a wavelength of the first illumination light, a wavelength of the second illumination light, or an average of wavelengths of the combination of the first illumination light and the second illumination light selected by the processor decreases.

11. A method for operating an endoscope system, comprising:
   acquiring a first image and a second image, the first image being obtained by imaging an observation target by using first illumination light, the second image being obtained by imaging the observation target by using second illumination light that is different from the first illumination light at a different timing from the first image;
   aligning the first image and the second image; and
   changing an accuracy of an alignment of the first image and the second image in accordance with at least a structure of interest to be observed,
   wherein the first illumination light and the second illumination light for imaging the observation target are selected in accordance with the structure of interest, and the accuracy of the alignment is changed in accordance with the first illumination light, the second illumination light, or a combination of the first illumination light and the second illumination light selected by the processor,
   wherein the accuracy of the alignment increases as a wavelength of the selected first illumination light, a wavelength of the selected second illumination light, or an average of wavelengths of the combination of the selected first illumination light and the selected second illumination light decreases.

* * * * *